US007967738B2

(12) United States Patent  
Dauterive

(10) Patent No.: US 7,967,738 B2  
(45) Date of Patent: Jun. 28, 2011

(54) THERAPEUTIC EXERCISE APPARATUSES

(76) Inventor: Ross Dauterive, Las Vegas, NV (US)

( * ) Notice: Subject to any disclaimer, the term of this patent is extended or adjusted under 35 U.S.C. 154(b) by 0 days.

(21) Appl. No.: 12/705,263

(22) Filed: Feb. 12, 2010

(65) Prior Publication Data

US 2010/0204027 A1 Aug. 12, 2010

Related U.S. Application Data

(60) Provisional application No. 61/152,059, filed on Feb. 12, 2009, provisional application No. 61/227,886, filed on Jul. 23, 2009.

(51) Int. Cl.
*A63B 26/00* (2006.01)
(52) U.S. Cl. ...................................................... 482/145
(58) Field of Classification Search .................. 482/145, 482/148, 139, 91, 51; 5/630, 648; 602/24; D24/190
See application file for complete search history.

(56) References Cited

U.S. PATENT DOCUMENTS

| | | | |
|---|---|---|---|
| 3,216,738 A | | 11/1965 | Bockus |
| 3,992,057 A | | 11/1976 | Studebaker |
| 4,372,299 A | * | 2/1983 | Fixel ................................ 602/24 |
| 4,796,881 A | | 1/1989 | Watterson |
| 4,805,605 A | * | 2/1989 | Glassman ........................ 602/24 |
| 4,815,732 A | | 3/1989 | Mahvi |
| 4,913,423 A | | 4/1990 | Farran et al. |
| 5,134,739 A | * | 8/1992 | Gaffe et al. ......................... 5/648 |
| 5,320,416 A | | 6/1994 | Kornberg |
| 5,451,092 A | | 9/1995 | Gray |
| 5,522,103 A | * | 6/1996 | Kier et al. .......................... 5/630 |
| 5,599,063 A | | 2/1997 | Lister et al. |
| D438,624 S | * | 3/2001 | Reina ............................ D24/190 |
| 6,427,426 B1 | | 8/2002 | Dunton et al. |
| 6,601,922 B2 | | 8/2003 | Doolan et al. |
| 6,752,414 B1 | | 6/2004 | Waldron et al. |
| 7,166,083 B2 | | 1/2007 | Bledsoe |
| 7,318,795 B2 | * | 1/2008 | Dauterive ...................... 482/148 |
| 2002/0115536 A1 | | 8/2002 | Hojo et al. |
| 2002/0198090 A1 | | 12/2002 | McKinney |

(Continued)

OTHER PUBLICATIONS

Patterson Medical Products, Inc., Rolyan Abduction Pillow Vinyl-Coated, 2010, http://www.sammonspreston.com/app.aspx?cmd=get_product&id=97097.

Patterson Medical Products, Inc., Wedge Flex Abduction Pillow, 2010, http://www.sammonspreston.com/app.aspx?cmd=get_product&id=97108.

*Primary Examiner* — Lori Baker
(74) *Attorney, Agent, or Firm* — Tucker Ellis & West LLP

(57) ABSTRACT

Exercise apparatus for use by handicapped persons for exercising their hips and legs. In one embodiment, an apparatus with a supporting structure and a seat mounted on the supporting structure. A cushion comprising a pad for splaying the knees of a user is mounted on the supporting structure. In another embodiment, there is a docking station suitably adapted for wheelchair users with a supporting structure protruding therefrom. A cushion is mounted on the protrusion for splaying the knees of the user. In yet another embodiment, a semispherical shaped seat is mounted on a supporting structure that can be adjusted to position a user near a handlebar structure with a supporting structure protruding therefrom. A cushion is mounted for splaying the knees of the user. Optionally, the cushions in the example embodiments may further comprise a patella pad. A knee spreader ball detached from the exercise apparatus permits training without the fixed cushion and, in a further form permits transport of a user without tangling the feet of the user.

11 Claims, 15 Drawing Sheets

U.S. PATENT DOCUMENTS

| | | |
|---|---|---|
| 2003/0137167 A1 | 7/2003 | Napell |
| 2003/0146601 A1 | 8/2003 | Gutierrez |
| 2005/0067861 A1 | 3/2005 | Avihod |
| 2005/0261114 A1 | 11/2005 | Heitzman et al. |

* cited by examiner

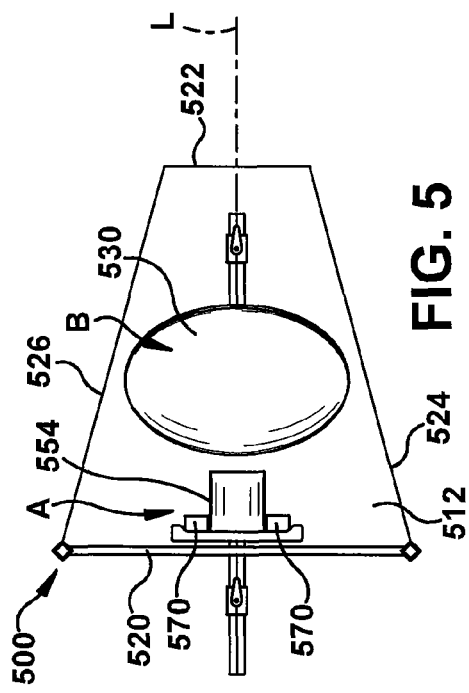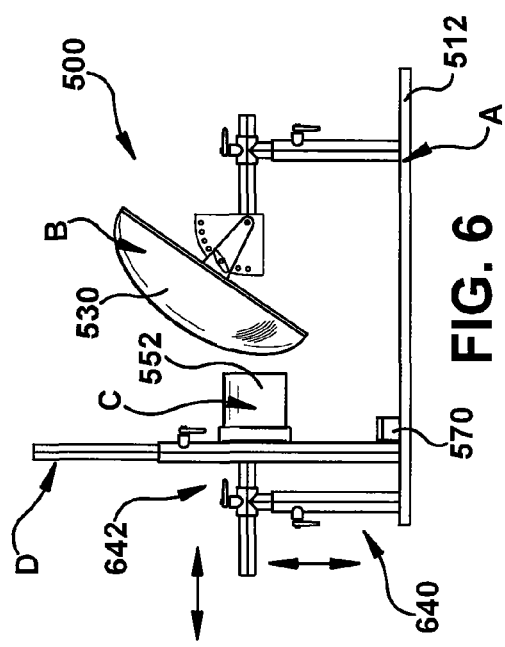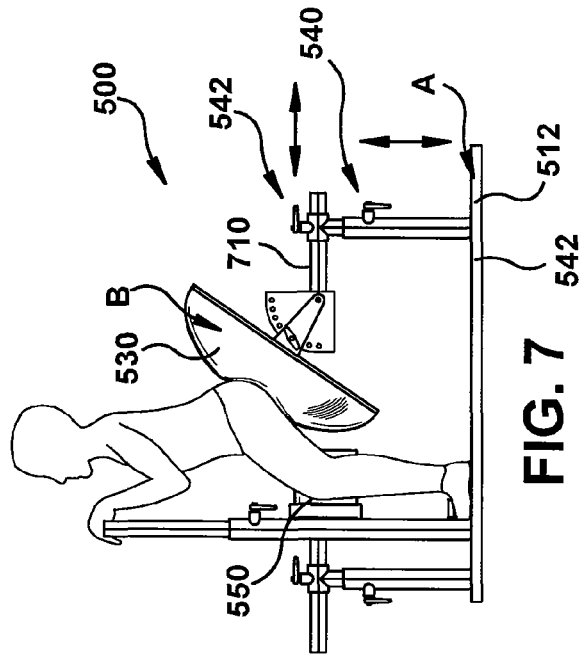

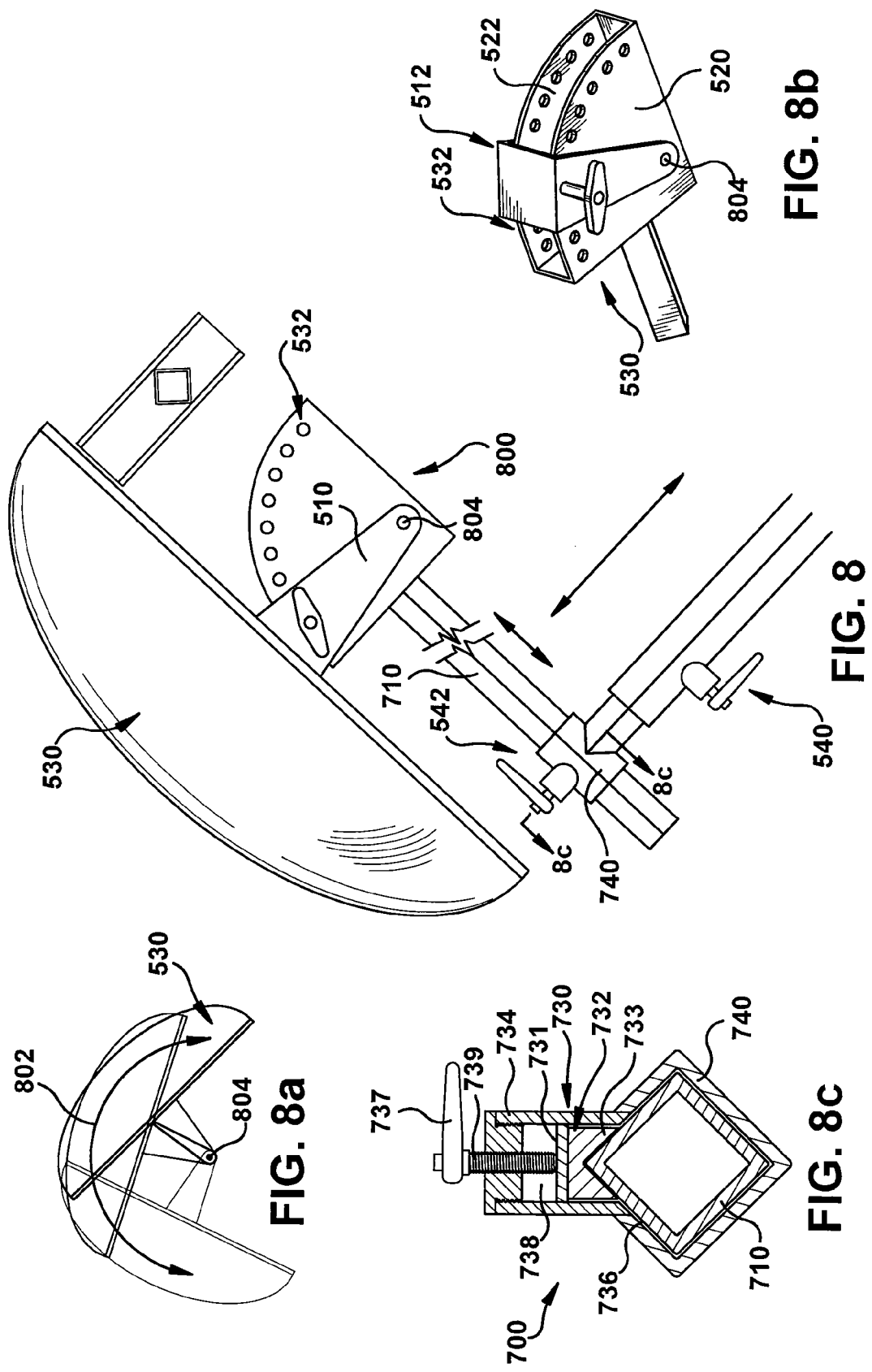

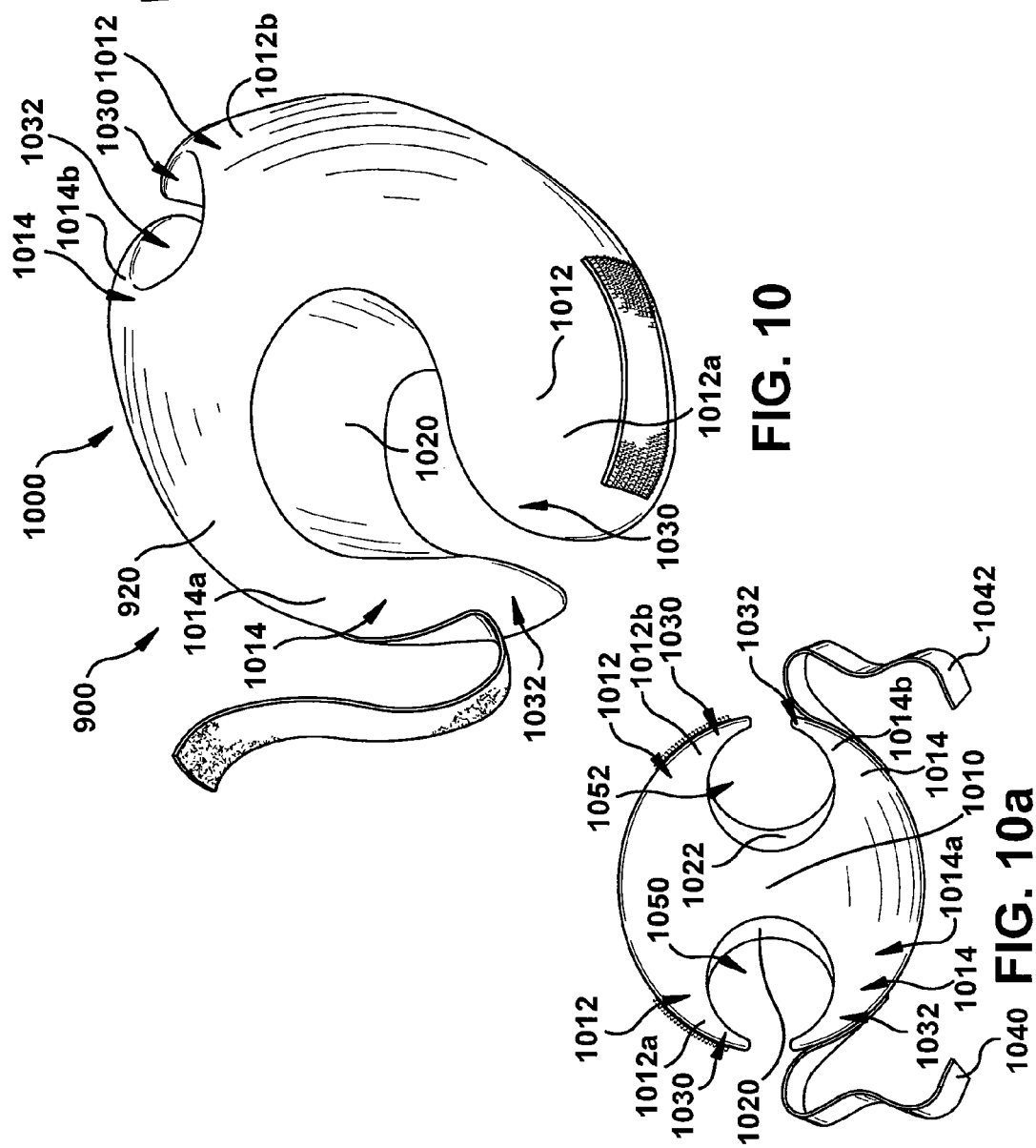

THERAPEUTIC EXERCISE APPARATUSES

CROSS-REFERENCE TO RELATED APPLICATIONS

This application claims the benefit of priority of U.S. Provisional Application No. 61/152,059 filed Feb. 12, 2009, and U.S. Provisional Application No. 61/227,886 filed on Jul. 23, 2009. All of the U.S. Provisional Application No. 61/152,059 is incorporated herein by reference.

This application is related to U.S. application Ser. No. 11/170,512 filed on Jun. 29, 2005, now U.S. Pat. No. 7,318, 795.

BACKGROUND OF THE INVENTION

The present disclosure relates generally to exercise devices and methods and more specifically to methods and apparatuses for enabling handicapped persons to exercise hips and legs to help prevent hip dislocation and muscle atrophy.

Handicapped children, particularly those with cerebral palsy typically suffer trismatic spasms which may eventually dislocate the femur from the hip sockets. Remedies for this problem include major surgery every two to three years. Thus, the need exists for systems and methods that enable a handicapped person to exercise their hips and legs to help prevent hip dislocation and muscle atrophy.

SUMMARY OF THE INVENTION

The following presents a simplified overview of the example embodiments in order to provide a basic understanding of some aspects of the example embodiments. This overview is not an extensive overview of the example embodiments. It is intended to neither identify key or critical elements of the example embodiments nor delineate the scope of the appended claims. Its sole purpose is to present some concepts of the example embodiments in a simplified form as a prelude to the more detailed description that is presented later.

In accordance with an aspect of the present invention, there is provided herein an apparatus wherein a handicapped person is securely and correctly positioned so that with little assistance they can exercise their hips and/or legs. In accordance with a further aspect, there is provided herein an apparatus wherein the legs of a handicapped person are securely and correctly positioned to prevent tangling so that the handicapped person may be more easily carried or otherwise transported by an assistant.

In accordance with an example embodiment, there is disclosed herein, an exercise apparatus comprising a base, a supporting structure mounted to the base and a seat mounted on the supporting structure. A cushion configured to splay the knees of a user is mounted on the supporting structure. In particular embodiments, the cushion comprises a patella pad. A handlebar or other structure is mounted on the base that allows a user using the apparatus to pull themselves up form the seat, while the cushion splays the knees of the user. A vertical position of the handlebar, vertical and horizontal positions of the seat, and vertical and horizontal positions of the cushion are each selectively adjustable to accommodate users of varying sizes.

In accordance with further example embodiments, there are disclosed herein, exercise apparatus suitably configured to dock with a wheelchair and enable a wheelchair bound user to exercise. The exercise apparatus comprise a base, a handlebar structure mounted to the base, a cushion mounted on a support structure mounted on the base so that the cushion is protruding in front of the handlebar structure, is configured to splay the knees of a user. In particular embodiments, the cushion comprises a patella pad. The handlebar structure allows a user using the apparatus to pull themselves up form their wheelchair, while the cushion splays the knees of the user. In other embodiments the cushion is detached from the base and from the seat wherein the cushion is provided in the form of a spheroid with surfaces defined by opposite outer sides configured to engage the inner legs of the user wherein the spheroid cushion is selectively securely attached with the user between the user's legs to splay the knees of the user during therapy or exercise using the handlebar and base structures. In further embodiments, a wheelchair pad is adapted to selectively attach with the exercise apparatus and is configured to support a wheelchair thereon. The pad helps maintain the wheelchair in a selected substantially fixed position relative to the exercise apparatus.

In accordance with still further example embodiments, the free detached spheroid cushion is a spheroid transport cushion including handle means for adapting the cushion to be gripped by an associated therapist or assistant to aid in transporting the handicapped user between selected locations. In one form the handle means include flexible straps attached with the cushion. The spheroid transport cushion helps maintain the user's legs in a fixed relative position to prevent the user's legs from becoming mutually tangled during transportation.

In accordance with a yet further example embodiment, there is disclosed herein, an exercise apparatus comprising a base a supporting structure mounted to the base and a handlebar or other structure is mounted on the base that allows a user using the apparatus to pull themselves up. A semispherical seat is mounted on the supporting structure. The supporting structure may employ levers or other devices that enable the position of the seat to be adjusted. A vertical position of the handlebar, vertical and horizontal positions of the semispherical seat, and vertical and horizontal positions of the cushion are each selectively adjustable to accommodate users of varying sizes.

BRIEF DESCRIPTION OF THE DRAWINGS

The accompanying drawings incorporated herein and forming a part of the specification illustrate the example embodiments.

FIG. 3a is a cross sectional view taken along line 3a-3a of FIG. 3 showing a cushion positioning device.

FIG. 5 is a top perspective view of a therapeutic exercise apparatus employing a semispherical ball shaped seat and a knee pad.

FIG. 6 is a left side view of the therapeutic exercise apparatus illustrated in FIG. 5.

FIG. 7 is side view of the therapeutic exercise apparatus of FIGS. 5 and 6 and illustrated with a user.

FIG. 8 is a side view of the ball seat support portion of the therapeutic exercise apparatus illustrated in FIGS. 5-7.

FIG. 8a is a simplified side view of the ball shaped seat portion of the therapeutic exercise apparatus illustrating a range of positions.

FIG. 8b is a side view of a pivot support system for the ball seat portion of the therapeutic exercise apparatus illustrated in FIG. 8.

FIG. 8c is a cross sectional view taken along line 8c-8c of FIG. 8 showing a seat positioning device.

FIG. 10 is a perspective view of the spheroid knee spreader ball of the therapeutic exercise apparatus FIG. 9.

FIG. 10a is a top view of the knee spreader ball of FIG. 10.

FIG. 10b is a front view of the knee spreader ball of FIG. 10 illustrated in use with a user.

DESCRIPTION OF EXAMPLE EMBODIMENTS

Figure 1:
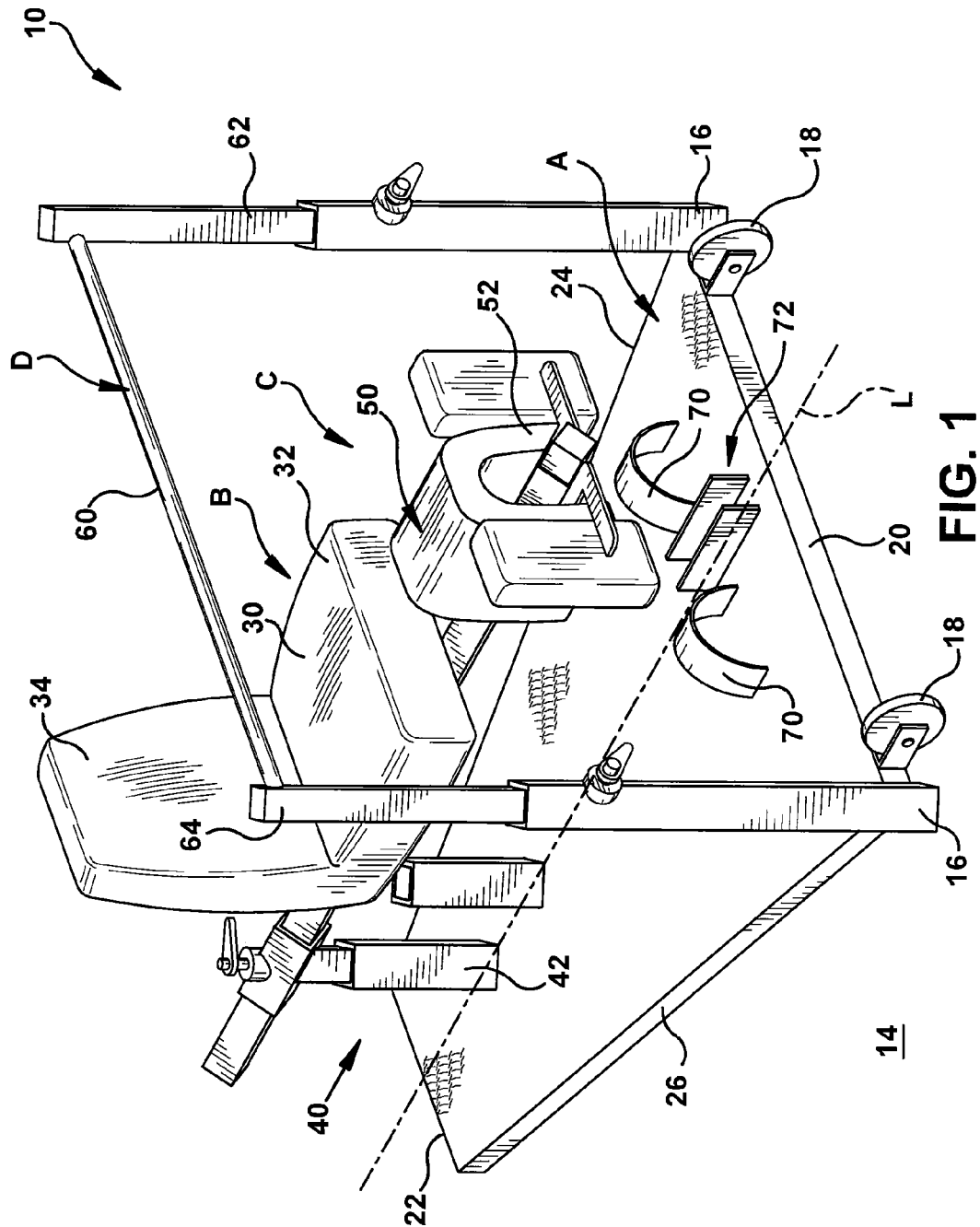
FIG. 1 is a perspective view of an exercise and therapy apparatus in accordance with an example embodiment.

This description provides examples not intended to limit the scope of any appended claims of applications claiming priority to this application. The figures generally indicate the features of the examples, where it is understood and appreciated that like reference numerals are used to refer to like elements. Reference in the specification to "one embodiment" or "an embodiment" or "an example embodiment" means that a particular feature, structure, or characteristic described is included in at least one embodiment described herein and does not imply that the feature, structure, or characteristic is present or necessary in all embodiments described herein.

Referring to FIG. 1 there is illustrated a therapy and exercise device 10 suitably adapted for enabling a crippled or otherwise handicapped persons to exercise hips and legs to prevent hip dislocation and muscle atrophy. The device 10 includes a base portion A for permitting the device 10 to rest stably on the floor 14 during use and storage of the device. A seat portion B is disposed in a raised vertical relationship relative to the base portion A, and a knee spreader portion C is disposed in a raised vertical relationship relative to the base portion A and further in a spaced apart forwardly and horizontally relative to the seat portion B. In the example embodiments, preferably, the vertical positioning of the seat portion B relative to the base portion A is adjustable within a predetermined adjustment range to accommodate users having different lengths of lower legs. Similarly, in the example embodiments, preferably, the vertical and/or horizontal positions of the knee spreader portion C relative to the base portion A and/or relative to the seat portion B are adjustable to within predetermined adjustment ranges to accommodate users having different lengths of upper legs. In one example embodiment, the knee spreader portion C is detachable from the base A and seat B portions of the exercise device 10. In another example embodiment, the knee spreader portion C is detached from the base A and seat B portions of the exercise device 10 and is freely carried between the knees of the user during therapy or exercise. A grippable boom portion D is disposed at a location relative to the base, seat, and knee spreader portions to enable a user to manually grasp the grippable boom portion D and, by using the arms, to raise and lower the body relative to the base and seat portions with the knee spreader holding the knees in a relatively splayed position during the raising and lowering movements. A foot securing portion E is provided on the base portion A for selectively assisting in fixing the users feet relative of the base portion A during use.

Figure 2:
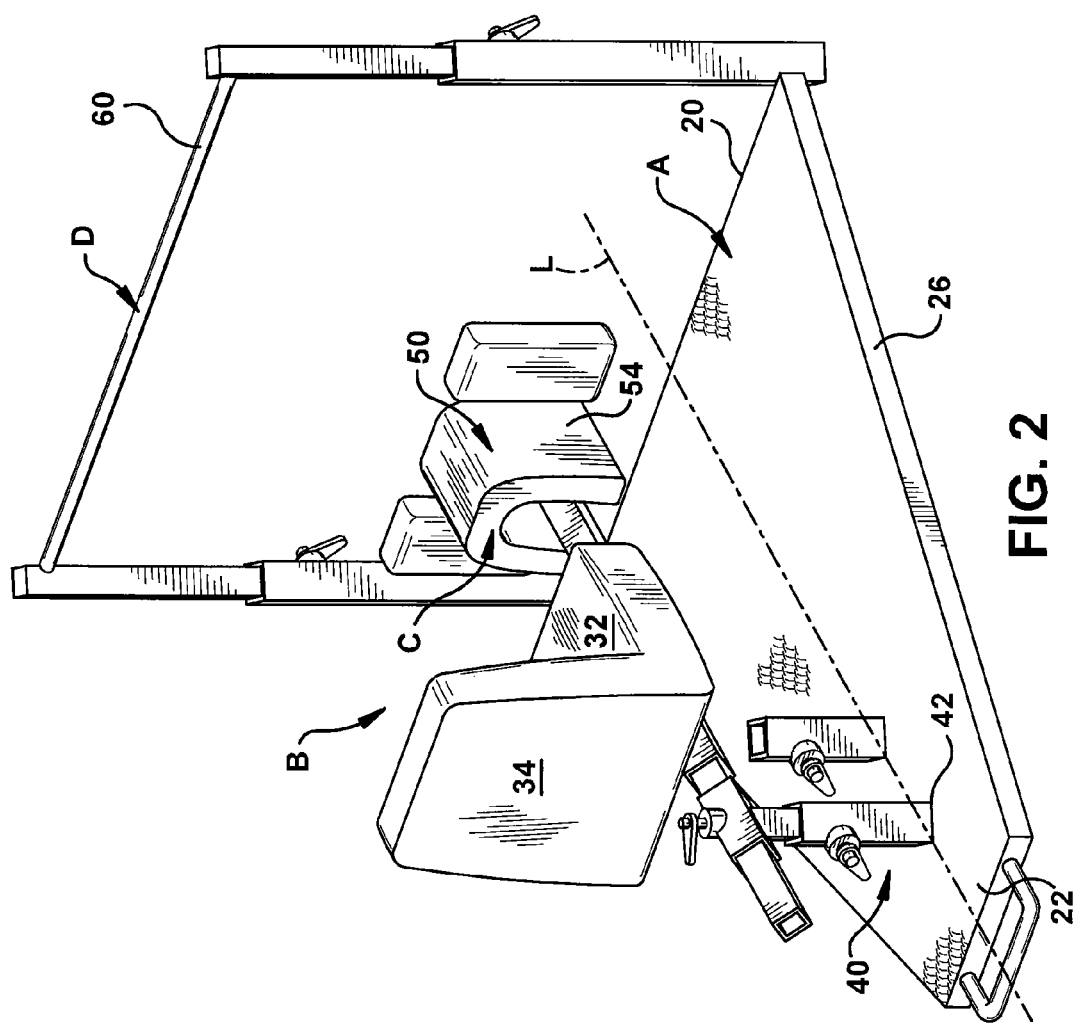
FIG. 2 is a perspective view of the apparatus in FIG. 1 with the seat raised and the knee spreader raised and extended from the seat.

In the example embodiment of FIGS. 1 and 2, the base portion A of the therapeutic exercise apparatus 10 comprises a flat substantially planar base 12 configured to rest stably on an associated floor 14 by means of a set of downwardly directed adjustable legs 16. Rubber cushions may be used or a flat interface of rubber or any other resilient material may be provided on the bottom surface of the base 12 to help support and secure the base relative to the floor during use of the therapy device. A pair of roller wheels 18 are coupled with a forward edge 20 the base 12 at locations suitable to enable the therapy device 10 to be tipped forward about an axis G defined by axles of the wheels for easily moving the device relative to the floor 14 such as when moving the device to or from storage. The base 12 further includes a rearward edge 22 and left 24 and right 26 edges whereby the base has a substantially trapezoidal and near rectangular shape. It is to be appreciated that the base may have other shapes and configurations as well. A longitudinal axis L is defined by the base 12 along a line substantially bisecting the base 12 and extending between the forward edge 20 and the rearward edge 22.

The seat portion B of the therapy device 10 includes in the example embodiment a seat 30 supported vertically relative to the base 12 by an upstanding support member 40. Preferably, the upstanding support member 40 extends from the base 12 in a direction substantially perpendicular to a plane defined by the base 12 and at a first position 42 along the longitudinal axis L. The seat 30 includes a lower portion 32 configured to support the buttocks of an associated user of the exercise apparatus relative to the base 12 and a back support portion 34 for engaging the user's back while seated on the lower portion. In the illustrated embodiment, the first position 42 of the elongate support member 40 is about ¼ the distance from the rearward edge 22 to the forward edge 20 along the longitudinal axis L.

The knee spreader portion C of the illustrated example therapy device 10 includes a cushion 50 disposed forwardly of the seat 30, preferably at a location whereby a user of the device may engage his legs with the cushion while sitting in the seat and, more preferably for exercise and therapy purposes, at a location whereby a user of the device may engage his legs with the cushion while rising from and sitting into the seat. The cushion 50 has a generally upside down "U" shape in cross section in a plane generally perpendicular to the longitudinal axis L wherein a pair of lateral spaced apart side walls 52, 54 are configured to engage the inside of the user's legs below the knees when seated in the seat 30. The side walls 52, 54 are generally planar and are disposed vertically or perpendicular relative to the plane defined by the base 12. Cushions having other shapes may be used as well including for example cushions having other one or more surfaces adapted to engage selected other portions of the users legs as may be necessary or desired. In one embodiment, the cushion includes one or more patella pads (FIGS. 3 and 4) for selectively engaging the patella of the The seat B and knee spreader C portions of the example embodiments including the embodiment of FIGS. 1 and 2 can accommodate users of varying sizes. To that end, preferably, the location of the seat 30 relative to the base 12 is adjustable vertically so that the seat may be located in a selected one of a plurality of raised or lowered positions relative to the base 12. Similarly, to further accommodate users of varying sizes, the location of the cushion 50 relative to the base 12 is adjustable vertically in a manner to be described in greater below so that the cushion may be located in a selected one of a plurality of raised or lowered positions relative to the base 12 and, further, the location of the cushion 50 relative to the seat 30 is adjustable horizontally in a manner to be described in greater below so that the cushion may be located in a selected one of a plurality of forward or rearward positions relative to the seat 30 by movement thereof along a line substantially in parallel with the longitudinal axis L. In a still further embodiment, the distance between the side walls 52, 54 is adjustable for users of varying girth.

The grippable boom portion D includes a handrail 60 supported in the illustrated example embodiment by a pair of spaced apart struts 62, 64 which extend vertically upwardly from the base 12 to a position over the seat 30 relative to the base 12. Although two struts 62, 64 are shown, any form of support for the handrail may be provided. In any case, however, preferably, the handrail 60 is supported at approximately the location illustrated in the Figures by the one or more struts or by other means relative to the base, seat, and knee spreader portions to enable a user to manually grasp the handrail 60 and, by using the arms, raise and lower the body relative to the base and seat portions. In one embodiment, the grippable boom portion D includes a ring on the end of a rope supported from above by an associated overhead ceiling, another similar or cooperating associated apparatus, or the like.

The foot retaining portion E includes a pair of stirrups 70 in the example embodiment affixed by suitable means on the base 12 in a spaced apart relationship on opposite sides of the longitudinal axis L thereof. The stirrups 70 are preferably formed of loops of flexible metal or any other material and are configured to hold the feet of the associated user of the exercise apparatus 10 in a substantially fixed relationship relative to the base member 12 so that the knees of the associated user are splayed out by the cushion 50 while using the apparatus by selectively gripping on the grippable portion of the handrail 60 and moving relative to the seat 30. Essentially, the cushion 50 holds the knees in a relatively splayed position during the raising and lowering movements. Further, a pair of upwardly directed generally planar foot positioning walls 72 are provided on the base 12 between the pair of stirrups 70 and on opposite sides of the longitudinal axis L. The foot positioning walls 72 help prevent the user's feet from undesirable inward movement towards each other during exercise and/or therapy.

Essentially, the positioning walls block ingress of the user's feet into the area defined between the walls along the longitudinal axis L. This assists in aligning the user's body and in particular assists in aligning the user's legs in desired relative positions with the apparatus 10 during therapy and/or exercise.

Figure 3:
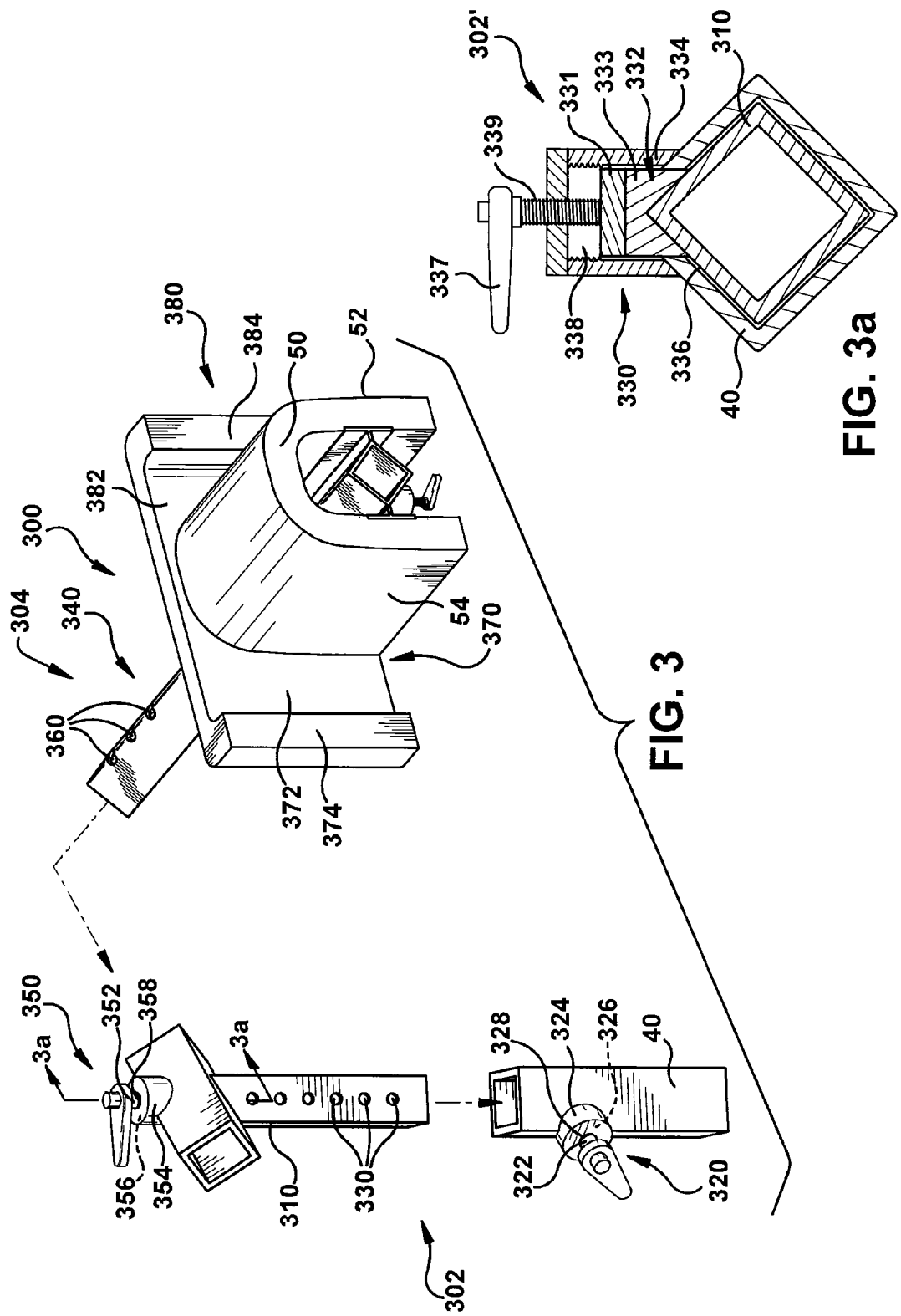
FIG. 3 is a perspective view of a support and adjustment system for the seat and knee spreader of FIGS. 1 and 2 and with an integrated patella pad.

FIG. 3 is an exploded perspective view of an example positioning apparatus 300 in accordance with an embodiment including a seat positioning apparatus 302 for positioning the seat 30 at a selected one of a plurality of positions relative to the base 12, and a cushion positioning device 304 for positioning the cushion 50 at a selected one of a plurality of positions relative to the base 12 and at a selected one of a plurality of positions relative to the seat 30. In the example illustrated, the cushion positioning device 304 is partially merged with the seat positioning apparatus 302 wherein the vertical height adjustment of the seat relative to the base effectively sets the same vertical height adjustment of the cushion 50 relative to the base. However, it is to be appreciated that in other equivalent embodiments, the cushion may be separately adjustable relative to the base and is further separately adjustable relative to the seat by merely replicating the set of apparatus 302, 304 in a second independent positioning apparatus (not shown) dedicated exclusively to vertical and horizontal adjustment of the knee cushion pad.

The seat positioning apparatus 302 includes an interface member 310 configured to be carried by the seat 30 such as by attachment thereto using suitable fasteners or the like (not shown), and a locking device 320 for selectively holding the interface member 310 and the seat 30 coupled therewith at selectable positions relative to the upstanding support member. The locking device 320 of the example embodiment includes a pin member 322 received in an enlarged boss 324 disposed adjacent a passageway (not shown) defined by the upstanding support member 40. The boss 324 defines an elongate passageway 326 therein configured to receive the pin member 322 therein. In its preferred form, the pin member 322 is inwardly biased relative to the boss 324 and support member 40 by a spring 328 and, further, is of adequate length to extend through the passageway (not shown) defined by the upstanding support member 40 for engagement with a selected one of a plurality of positioning detents 330 formed linearly along the longitudinal axis of the interface member 310. As can be seen from the Figure, the interface and support members 310, 40 are formed for relative mutual telescopic connection so that the relative length of the seat positioning apparatus 302 in a direction perpendicular to the base 12 (FIGS. 1 and 2) can be adjusted.

Similarly, the cushion positioning apparatus 304 includes an interface member 340 configured to carry the cushion 50 such as by attachment thereto using suitable fasteners or the like (not shown), and a locking device 350 for selectively holding the interface member 340 and the cushion 50 coupled therewith at selectable extended and retracted positions relative to the upstanding support member. The locking device 350 of the example embodiment includes a pin member 352 received in an enlarged boss 354 disposed adjacent a passageway (not shown) defined by the seat interface member 310. The boss 354 defines an elongate passageway 356 therein configured to receive the pin member 352 therein. In its preferred form, the pin member 352 is inwardly biased relative to the boss 354 by a spring 358 and, further, is of adequate length to extend through the passageway (not shown) defined by the seat interface member 310 for engagement with a selected one of a plurality of positioning detents 360 formed linearly along the longitudinal axis of the interface member 310. As can be seem from the Figure, the interface and support members 340, 310 are formed for relative mutual slidable connection so that the relative length of the cushion positioning apparatus 304 in a direction parallel to the base 12 and longitudinal axis L (FIGS. 1 and 2) can be adjusted as necessary or desired to accommodate users of varying sizes.

The cushion 50 of FIG. 3 includes an integrated set of patella pads 370, 380 extending in opposite directions from the cushion in a plane perpendicular to the longitudinal axis L. In an example embodiment, the patella pads 370, 380 each respectively include a forward knee engagement surface 372, 382 configured and disposed in the apparatus to engage the front region of the knees of the user, and outer knee engagement surfaces 374, 384 configured and disposed in the apparatus to engage the outer side regions of the knees of the user.

In a further example embodiment, one or both of the locking devices 320, 350 provide a wider range of selective adjustability for the seat and cushion, respectively and wherein, as illustrated for example in FIG. 3a, a modified seat or cushion positioning apparatus 302' includes a v-plunger apparatus 330 for selectively clamping respective portions of the positioning apparatus 300 at selected locked positions. The positioning apparatus 302' includes v-plunger member 332 received in an enlarged boss 334 disposed adjacent a passageway 336 defined by the upstanding support member 40. The boss 334 defines an elongated passageway 338 therein configured to receive the v-plunger 332. In its preferred form, the v-plunger 332 is selectively inwardly biased relative to the boss 334 and support member 40 by a handled screw 339 and, further, is of adequate length to extend through the passageway 336 defined by the upstanding member 40 for engagement by the v-plunger 332 against the interface member 310 while the interface member 310 is positioned at any desired point linearly along the longitudinal axis of the upstanding member 40. In its preferred form, the v-plunger 332 includes a first portion 331 formed of a substantially rigid material such as, for example, steel, and a second portion 333 formed of a substantially inert material having desirable friction and non-compressibility properties such as, for example, Teflon. The v-plunger apparatus 330 is used by twisting the handle 337 in turn driving the screw 339 therewith and urging the v-plunger 332 forward relative to the enlarged boss 334, whereby the second portion 333 of the v-plunger 332 engages the interface member 310 and compresses the interface member 310 against the upstanding member 40, thereby holding the interface member 310 and the upstanding member 40 in a relative locked position. Essentially, the interface member 310 and the upstanding member 40 are held in the selected relative position by friction.

Figure 4:
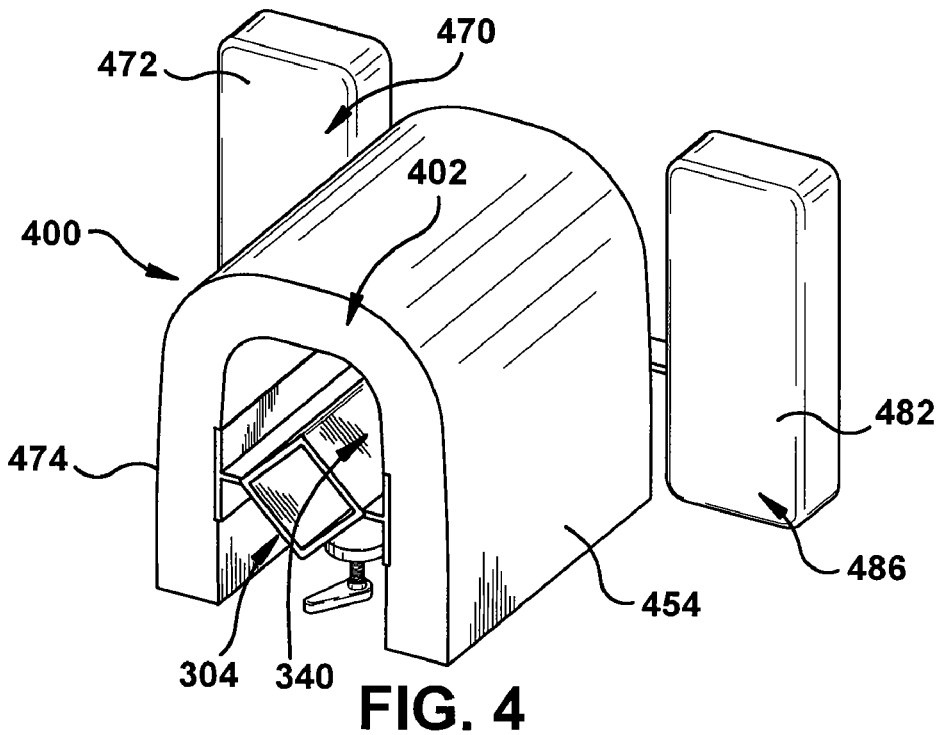
FIGS. 4, 4a, and 4b are perspective, front, and top views of a further embodiment of a knee spreader with a pair of patella pads spaced from the central cushion.
Figure 4A:
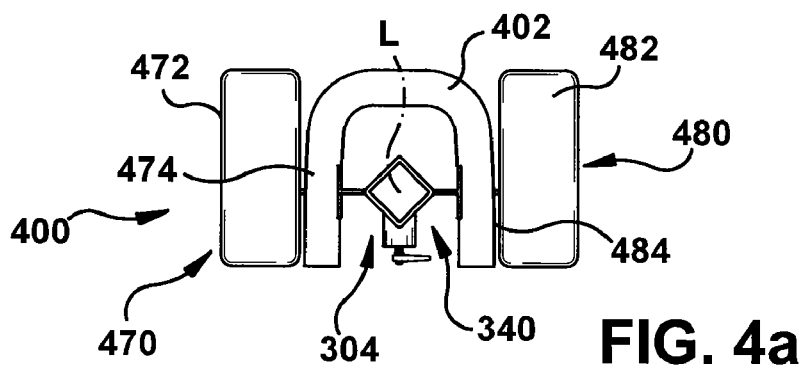
Figure 4B:
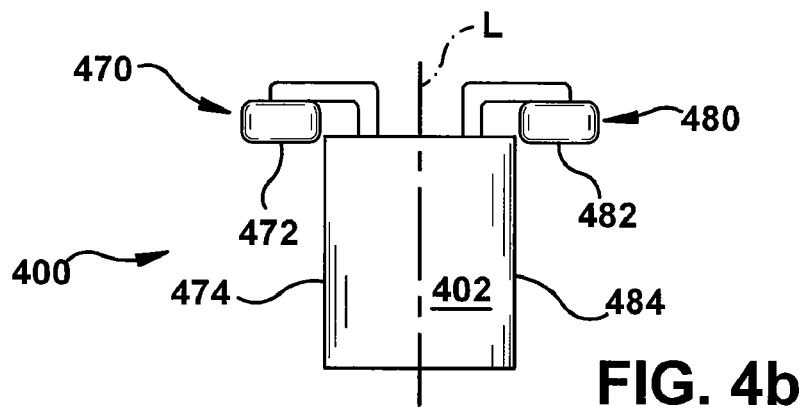

FIG. 4 illustrates a further embodiment of a cushion 400 and a support system therefore similar to the support system of FIG. 3, wherein like numerals for the support system are used for similar surfaces but with a primed "'" notation. The cushion 400 of FIGS. 4, 4a, and 4b includes a set of spaced apart patella pads 470, 480 extending in opposite directions from the main or central cushion 402 in a plane perpendicular to the longitudinal axis L. In an example embodiment, the patella pads 470, 480 each respectively include a forward knee engagement surface 472, 482 configured and disposed in the apparatus to engage the front region of the knees of the user, and outer knee engagement surfaces 474, 484 configured and disposed in the apparatus to engage the outer side regions of the knees of the user.

Turning now to FIGS. 5-7, a further example embodiment of a therapeutic exercise apparatus 500 is illustrated in top, side, and side with user views, respectively. Similar to the example embodiment of FIGS. 1-4, the illustrated apparatus 500 of FIGS. 5-7 includes a base portion A for permitting the device 500 to rest stably on the floor 14 during use and storage of the device. A seat portion B is disposed in a raised vertical relationship relative to the base portion A, and a knee spreader portion C is disposed in a raised vertical relationship relative to the base portion A. The knee spreader portion C is disposed in a spaced apart position forwardly and horizontally relative to the seat portion B and, further, the seat portion B is disposed in a spaced apart position forwardly and horizontally relative to the knee spreader portion C. In the example embodiment, preferably, the vertical positioning of the seat B and spreader C portions relative to the base portion A are each independently adjustable within predetermined adjustment ranges to accommodate users having different lengths of lower legs. Similarly, in the example embodiments, preferably, the horizontal positions of the seat B and knee spreader C portions relative to each other are separately and independently adjustable to within predetermined adjustment ranges to accommodate users having different lengths of upper legs. A grippable boom portion D is disposed at a location relative to the base A, seat B, and knee spreader portions C to enable a user to manually grasp the grippable boom portion D and, by using the arms, to raise and lower the body relative to the base and seat portions with the knee spreader holding the knees in a relatively splayed position during the raising and lowering movements. A foot securing portion E is provided on the base portion A for selectively assisting in fixing the users feet relative to the base portion A during use.

In the example embodiment of FIGS. 5-7, the base portion A of the therapeutic exercise apparatus 500 comprises a flat substantially planar base 512 configured to rest stably on an associated floor 514 by means of a set of downwardly directed adjustable legs (not shown). Rubber cushions (not shown) may be used or a flat interface of rubber or any other resilient material may be provided on the bottom surface of the base 512 to help support and secure the base relative to the floor during use of the therapy device. The base 512 further includes a rearward edge 522 and left 524 and right 526 edges whereby the base has a substantially trapezoidal and near rectangular shape. It is to be appreciated that the base may have other shapes and configurations as well. A longitudinal axis L is defined by the base 512 along a line substantially bisecting the base 512 and extending between the forward edge 520 and the rearward edge 522.

The seat portion B of the therapy device 500 includes in the example embodiment a partial-spherical seat 530 supported vertically relative to the base 512 by an upstanding support member 540 and supported horizontally relative to the base 512 by a laterally extending support member 550. Preferably, the upstanding support member 540 extends from the base 512 in a direction substantially perpendicular to a plane defined by the base 512 and at a first position 542 along the longitudinal axis L. The seat 530 includes a resilient and flexible convex portion 532 configured to support the buttocks of an associated user of the exercise apparatus relative to the base 512. A back support portion for engaging the user's back while seated on the lower portion is not necessary in the example embodiment as the flexible convex portion 532 enables exercise and promotion of core strength and fitness of the user. In the illustrated embodiment, the first position 542 of the elongate support member 540 is about ¼ the distance from the rearward edge 522 to the forward edge 520 along the longitudinal; axis L.

The knee spreader portion C of the illustrated example therapy device 500 includes a cushion 550 disposed forwardly of the seat 530, preferably at a location whereby a user of the device may engage his legs with the cushion while sitting in the seat and, more preferably for exercise and therapy purposes, at a location whereby a user of the device may engage his legs with the cushion while rising from and sitting into the seat. The cushion 550 has a generally upside down "U" shape in cross section in a plane generally perpendicular to the longitudinal axis L wherein a pair of lateral spaced apart side walls 552, 554 are configured to engage the inside of the user's legs below the knees when seated on the seat 530. The side walls 552, 554 are generally planar and are disposed vertically or perpendicular relative to the plane defined by the base 512. The cushion includes one or more patella pads 570, 580 for selectively engaging the patella of the user while using the apparatus 500. Cushions having other shapes may be used as well including for example cushions having other one or more surfaces adapted to engage selected other portions of the users legs as may be necessary or desired.

The seat B and knee spreader C portions of the example embodiments including the embodiment of FIGS. 5-7 can accommodate users of varying sizes. To that end, preferably, the location of the seat 530 relative to the base 512 is adjustable vertically and horizontally so that the seat may be located in a selected one of a plurality of raised or lowered positions relative to the base 512 and in a selected one of a plurality of extended or retracted positions relative to the cushion 550 and to the grippable boom portion D. Similarly, to further accommodate users of varying sizes, the location of the cushion 550 relative to the base 512 is adjustable vertically by a positioning apparatus 640 in a manner to be described in greater detail below so that the cushion 550 may be located in a selected one of a plurality of raised or lowered positions relative to the base 12 and, further, the location of the cushion 550 relative to the seat 530 and to the boom D is adjustable horizontally in a manner to be described in greater below so that the cushion may be located in a second positioning apparatus 642 in a selected one of a plurality of forward or rearward positions relative to the seat 530 and boom D by movement thereof along a line substantially in parallel with the longitudinal axis L. In a still further embodiment, the distance between the side walls 552, 554 of the cushion 550 is adjustable for users of varying girth.

The grippable boom portion D includes a handrail 560 supported in the illustrated example embodiment by a pair of spaced apart struts 562, 564 which extend vertically upwardly from the base 512 to a position over the seat 530 relative to the base 512. Although two struts 562, 564 are shown, any form of support for the handrail may be provided. In any case, however, preferably, the handrail 560 is supported at approximately the location illustrated in the Figures by the one or more struts or by other means relative to the base, seat, and knee spreader portions to enable a user to manually grasp the handrail 560 and, by using the arms, raise and lower the body relative to the base and seat portions. In one embodiment, the grippable boom portion D includes a ring on the end of a rope supported from above by an associated overhead ceiling, another similar or cooperating associated apparatus, or the like.

The foot retaining portion E includes a pair of stirrups 570 in the example embodiment affixed by suitable means on the base 512 in a spaced apart relationship on opposite sides of the longitudinal axis L thereof. The stirrups 570 are preferably formed of loops of flexible metal or any other material and are configured to hold the feet of the associated user of the exercise apparatus 500 in a substantially fixed relationship relative to the base member 512 so that the knees of the associated user are splayed out by the cushion 550 while using the apparatus by selectively gripping on the grippable portion of the handrail 560 and moving relative to the seat 530. Essentially, the cushion 550 holds the knees in a relatively splayed position during the raising and lowering movements. Further, a pair of upwardly directed generally planar foot positioning walls (not shown) may 72 be selectively provided on the base 512 between the pair of stirrups 570 and on opposite sides of the longitudinal axis L. The foot positioning walls help prevent the user's feet from undesirable inward movement towards each other during exercise and/or therapy. Essentially, the positioning walls block ingress of the user's feet into the area defined between the walls along the longitudinal axis L. This assists in aligning the user's body and in particular assists in aligning the user's legs in desired relative positions with the apparatus 500 during therapy and/or exercise.

In one example embodiment, the seat 530 is mounted on the seat positioning apparatus 302 by a tilt support system 800 shown in FIG. 8 for providing a range mounting options of the seat 530 relative to the seat positioning apparatus 302. In that way, the seat 530 may be selectively positioned in any one of a plurality of positions along an arc 802 such as illustrated for example in FIG. 8a. Accordingly, the seat may be tilted or pivoted about a pivot point 804 into a selected position as deemed necessary or desired by the user. The seat 530 in the illustrated embodiment is provided with a pair of spaced apart bracket members 510, 512 extending downwardly from the bottom thereof. Each of the bracket members defines a pair of spaced apart positioning holes configured to receive a corresponding set of fasteners (not shown) for selective connection with a set of spaced apart curved mounting brackets 520, 522 configured for attachment with the seat positioning apparatus 530 described above in connection with FIGS. 5-7. A corresponding set of spaced apart positioning holes 530, 532 are arranged on the curved mounting brackets 520, 522 in a manner that the seat 530 may be selectively mounted to the brackets 520, 522 at any selected position along the arc 802.

In a further example embodiment, one or more locking devices 540, 542, 640, 642 provide a wider range of selective adjustability for the seat and cushion, respectively and wherein, as illustrated for example in FIG. 8a, a modified seat or cushion positioning apparatus 700 includes a v-plunger apparatus 730 for selectively clamping respective portions of the positioning apparatus 542 at selected locked positions. The positioning apparatus 700 includes v-plunger member 732 received in an enlarged boss 734 disposed adjacent a passageway 736 defined by the seat support member 740. The boss 734 defines an elongated passageway 738 therein configured to receive the v-plunger 732. In its preferred form, the v-plunger 732 is selectively inwardly biased relative to the boss 734 and seat support member 740 by a handled screw 739 and, further, is of adequate length to extend through the passageway 736 defined by the seat support member 740 for engagement by the v-plunger 732 against the interface member 710 while the interface member 710 is positioned at any desired point linearly along the longitudinal axis of the seat support member 740. In its preferred form, the v-plunger 732 includes a first portion 731 formed of a substantially rigid material such as, for example, steel, and a second portion 733 formed of a substantially inert material having desirable friction and non-compressibility properties such as, for example, Teflon. The v-plunger apparatus 730 is used by twisting the handle 737 in turn driving the screw 739 therewith and urging the v-plunger 332 forward relative to the enlarged boss 334, whereby the second portion 333 of the v-plunger 732 engages the interface member 710 and compresses the interface member 710 against the seat support member 740, thereby holding the interface member 710 and the seat support member 740 in a relative locked position. Essentially, the interface member 710 and the seat support member 740 are held in the selected relative position by friction.

Figure 9A:
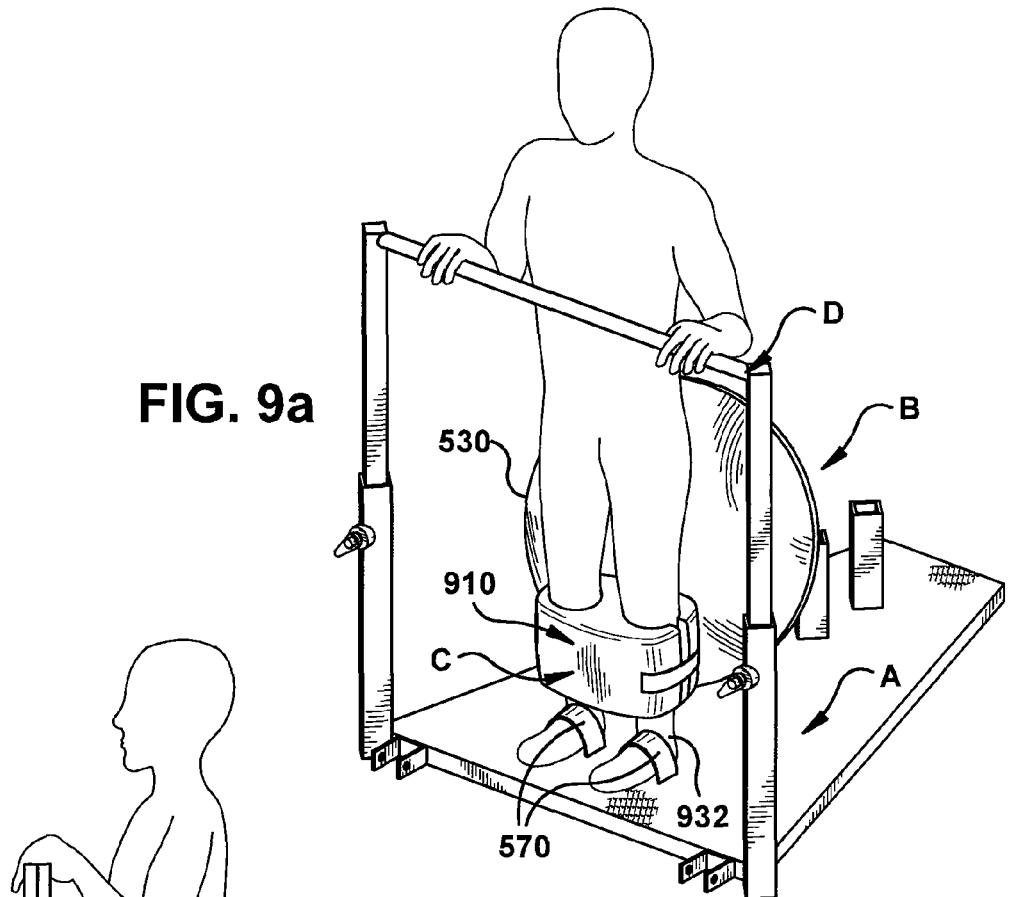
FIGS. 9 and 9a are side and perspective views of a therapeutic exercise apparatus employing a semispherical ball shaped seat and a free spheroid knee spreader ball in accordance with a further example embodiment illustrated with a user.
Figure 9:
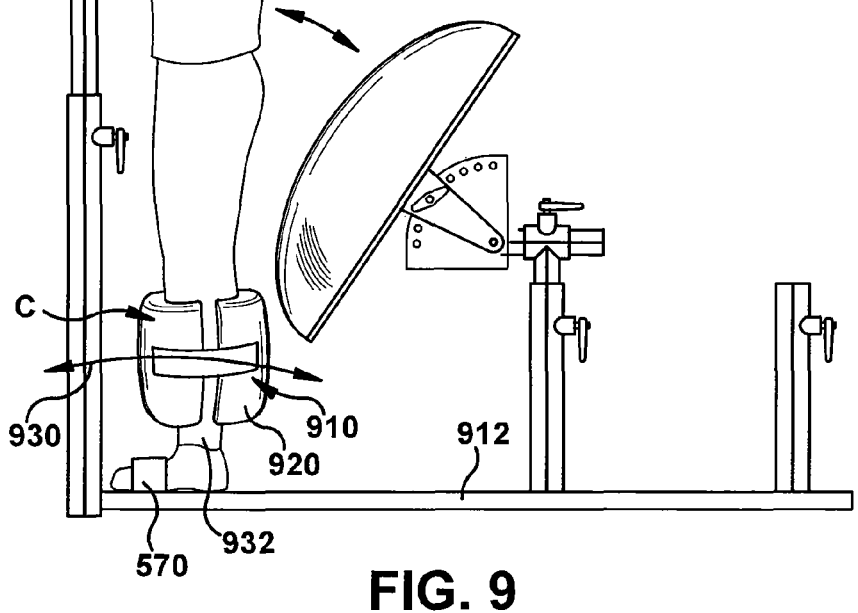

In a further example embodiment as shown in FIG. 9, the therapeutic exercise apparatus 900 of FIGS. 5-7 is used with a spheroid training apparatus 910 in the form of a training ball 920. As can be seen, the training apparatus 910 is detached from the exercise apparatus 900 and is instead carried between the legs of the user during therapy and/or exercise. The ball is selectively securely attached to the user's legs in a manner to be described below whereby the ball maintains the user's knees in a desired splayed condition while raising and lowering the user's body relative to the base 912 of the therapeutic exercise apparatus 900. In this way, the lower leg portions of the user's legs may move in an arc 930 relative to a pivot point 932 disposed near the user's ankles. The training ball 920 is effectively operative as the knee spreader portion C illustrated and described above, but without being fixed or otherwise connected with the other portions of the therapeutic training apparatus.

FIGS. 10 and 10a show perspective and top views of the therapeutic exercise apparatus 900 of FIG. 9, and FIG. 10b shows the apparatus in use on a user's legs in accordance with an example embodiment. As illustrated, the training ball 920 is a generally spheroid device 1000 including a central body portion 1010 with anterior 1012 and posterior 1014 leg stabilizing members extending outwardly from the central body portion 1010. In one preferred form, the ball is made of foam but it may also be made of plastic or foam covered with a rubberized material or the like. In the example embodiment, the central body portion has opposite first 1020 and second 1022 ends, the first end 1020 is configured to engage an inside portion of a first leg of the associated user (FIG. 10b), and the second end 1022 is configured to engage an inside portion of a second leg of the associated user (FIG. 10b). The anterior leg stabilizing members 1012 extend generally outwardly from the first and second ends of the central body portion 1010. A first anterior leg stabilizing member 1012a is configured to engage an anterior leg portion of the first leg of the associated user, and the second anterior leg stabilizing member 1012b is configured to engage an anterior leg portion of the second leg of the associated user. Similarly, a first posterior leg stabilizing member 1014a is configured to engage a posterior leg portion of the first leg of the associated user and a second posterior leg stabilizing member 1014b is configured to engage a posterior leg portion of the second leg of the associated user. In the example embodiment, the central body portion 1010 and the anterior 1012 and posterior 1014 leg stabilizing members collectively hold the knees of the associated user in a splayed relative orientation such as illustrated in FIG. 10b.

FIGS. 10 and 10a further illustrate outer leg stabilizing members 1030 and 1032 operatively coupled with the central body portion. A first set of outer leg stabilizing members 1030a, 1032a are configured to cooperatively engage an outside leg portion of the first leg of the associated user and hold the first leg of the associated user against the first end 1020 of the central body portion 1010. Similarly, a second set of outer leg stabilizing members 1030b, 1032b are configured to engage an outside leg portion of the second leg of the associated user and hold the second leg of the associated user against the second end 1022 of the central body portion 1010.

A first set of straps 1040 are provided on one side of the central body portion 1010 and, together with a second set of straps 1042 provided on the other side of the central body portion 1010 are configured to selectively assist in affixing the ball 920 to the legs of the user below the knees such as shown in FIG. 10b. The free ends of the straps 1040, 1042 carry a first portion of a loop and hook fastener and the outer surface of the body 920 carries the complementary portion of the loop and hook fastener system whereby the straps may be selectively opened to permit the reception of the user's legs into elongate channels 1050, 1052 defined in the body, and selectively releasably mutually attached for securing the user's legs in the channels for holding the knees in the splayed orientation such as shown in FIG. 10b.

Figure 12:
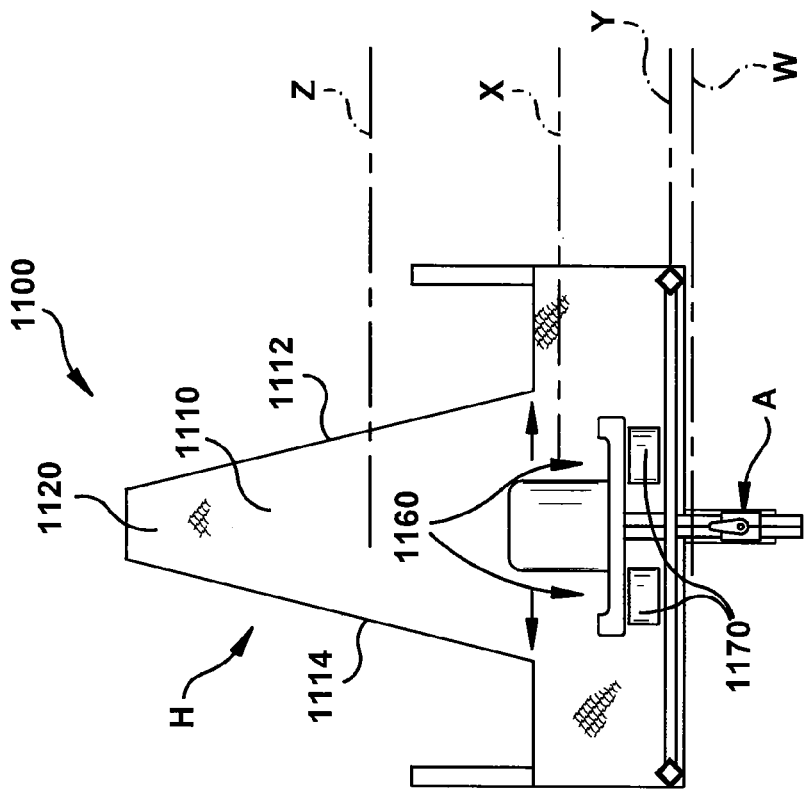
FIG. 12 is a top view of the therapeutic exercise apparatus illustrated in FIG. 11.
Figure 11:
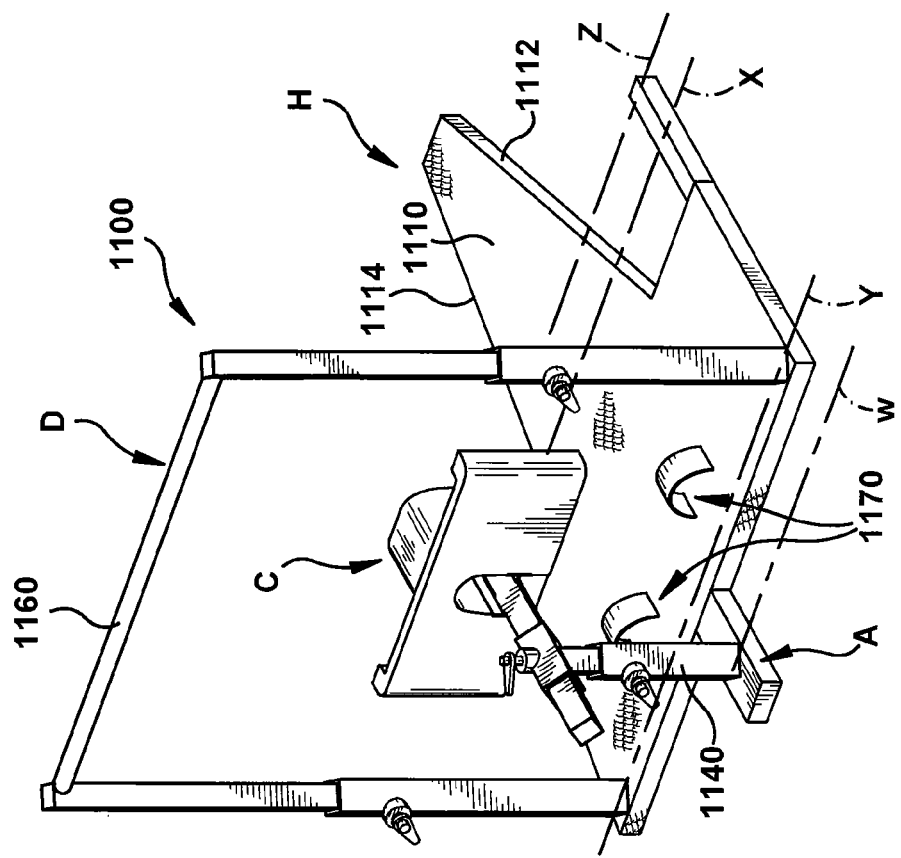
FIG. 11 is a perspective view of a therapeutic exercise apparatus configured as a docking station suitably adapted for a wheelchair bound user.

FIGS. 11 and 12 illustrate a further example embodiment of a therapeutic exercise system 1100 in accordance with a further embodiment. As shown there, a therapeutic exercise apparatus 1100 is configured as a docking station H suitable for a wheelchair bound user. This embodiment comprises a base portion A configured to hold stirrups E, a handlebar D, and a support structure for holding a knee spreader C. In particular embodiments, the knee spreader C includes a patella pad as illustrated herein. The base portion A in this embodiment includes a triangular shaped central base member 1110 having outer left 1112 and right 1114 edges. The outer edges define a truncated wedge 1120 configured to assist in guiding an associated wheelchair into areas adjacent the edges 1112, 1114 and on a side of the boom portion D opposite the knee spreader portion C and support thereof. This embodiment enables the user of the device to exercise without leaving his wheelchair wherein the chair may be rolled into the docking station area H adjacent apparatus.

In the embodiment illustrated, the base member A of the exercise apparatus 1100 defines a longitudinal axis L. An upstanding support member 1140 extends from the base member A at a first position W on the longitudinal axis L. A cushion C is operatively attached with the support member 1140 and is configured to engage the legs of the associated user of the exercise apparatus 1100. The cushion C is located relative to the support member 1140 at a second position X on the longitudinal axis L. A handrail D extends from the base member A and includes a grippable portion 1160 located above the cushion at a third position Y on the longitudinal axis L spaced from the first X and second Y positions on the longitudinal axis L. A user support member H is operatively coupled with the base member A and is adapted to rest stably on a floor. The user support member H is disposed at a fourth position Z on the longitudinal axis spaced from the second position X opposite the first position W and has spaced apart longitudinal foot support sections 1160 extending in parallel with the longitudinal axis. Each of the foot support sections 1160 includes stirrups 1170 for receiving a foot of a user in a substantially fixed relationship relative to the user support member while seated in an associated wheel chair adjacent the exercise apparatus so that the knees of the associated user are splayed out by the cushion while using the apparatus by selectively gripping on the grippable portion of the handrail and moving by standing and sitting relative to the handrail and associated wheelchair. The foot support sections include stirrups mounted on the user support member in a spaced apart relationship on opposite sides of the longitudinal axis, the stirrups being configured to loop around and hold the feet of the associated user of the exercise apparatus in the substantially fixed relationship relative to the user support member so that the knees of the associated user are splayed out by the cushion while using the apparatus by selectively gripping on the grippable portion of the handrail and moving by standing and sitting relative to the handrail and associated wheelchair.

Figure 13:
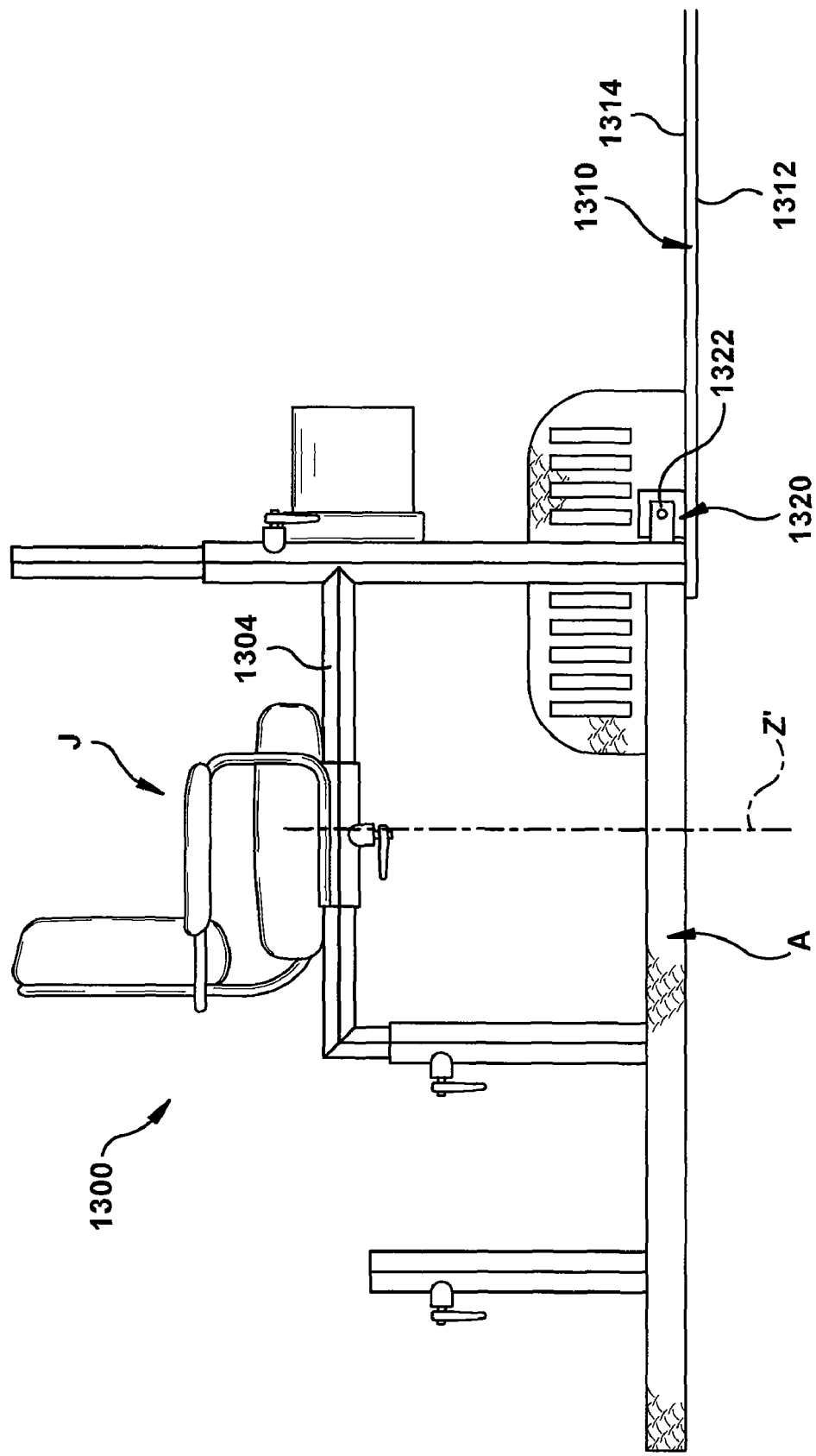
FIG. 13 is a side view of a therapeutic exercise apparatus configured as a docking station suitably adapted for a wheelchair bound user and including a therapist chair.

In the example embodiment of FIG. 13, a seat J is mounted relative to the upstanding support member on the longitudinal axis at a fifth position Z' between the first position and the handrail. The seat is configured to support the buttocks of an associated therapist second user of the exercise apparatus.

Figure 14:
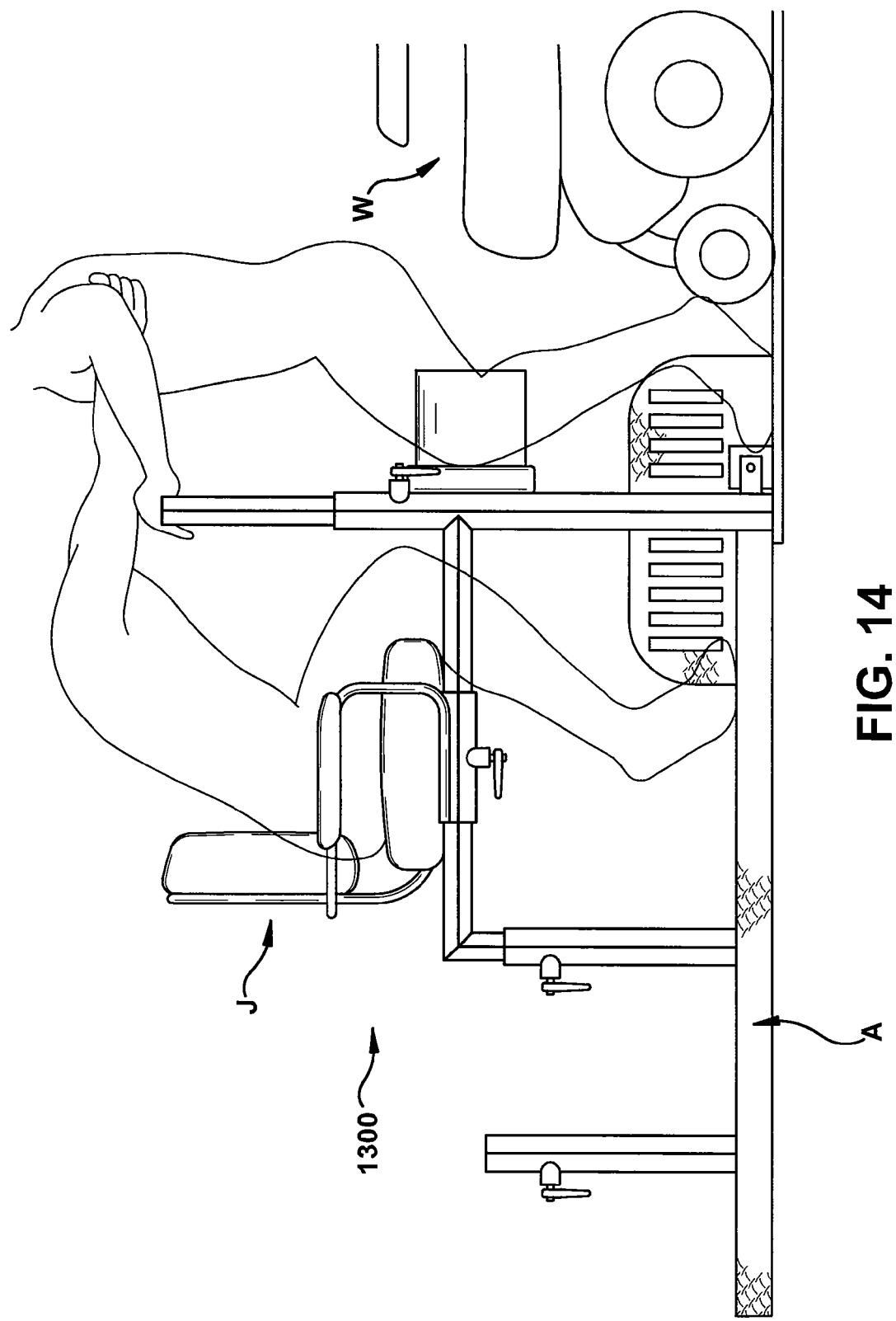
FIG. 14 is a side view of the therapeutic exercise apparatus of FIG. 13 illustrated with a user and with a therapist assisting the user.

In particular, FIG. 13 illustrates a further embodiment of a therapeutic exercise apparatus 1300 of the type shown in FIGS. 11 and 12 configured as a docking station suitable for a wheelchair bound user and including a therapist chair J operatively mounted on the support 1304 for the knee spreader portion C. FIG. 14 shows an associated therapist assisting an associated user in the apparatus 1300. As illustrated, the docking station H of the example embodiment includes a flat support member 1310 selectively attached with the base portion A by an attachment member 1320. In the example embodiment, the flat support member 1310 is a lightweight metal or plastic pad member 1314 configured to selectively receive and associated wheelchair thereon. The pad member 1314 assists in holding the associated wheelchair in a substantially fixed position relative to the base portion A during therapeutic or other use of the apparatus 1300. The support member 1310 is attached with the base portion A by an attachment member 1320, preferably in the form of a pivot attachment member 1322 whereby the support member 1310 may be selectively removed from attachment with the base portion A or pivoted upwardly as viewed in the Figure when the apparatus is not in use.

Figure 15:
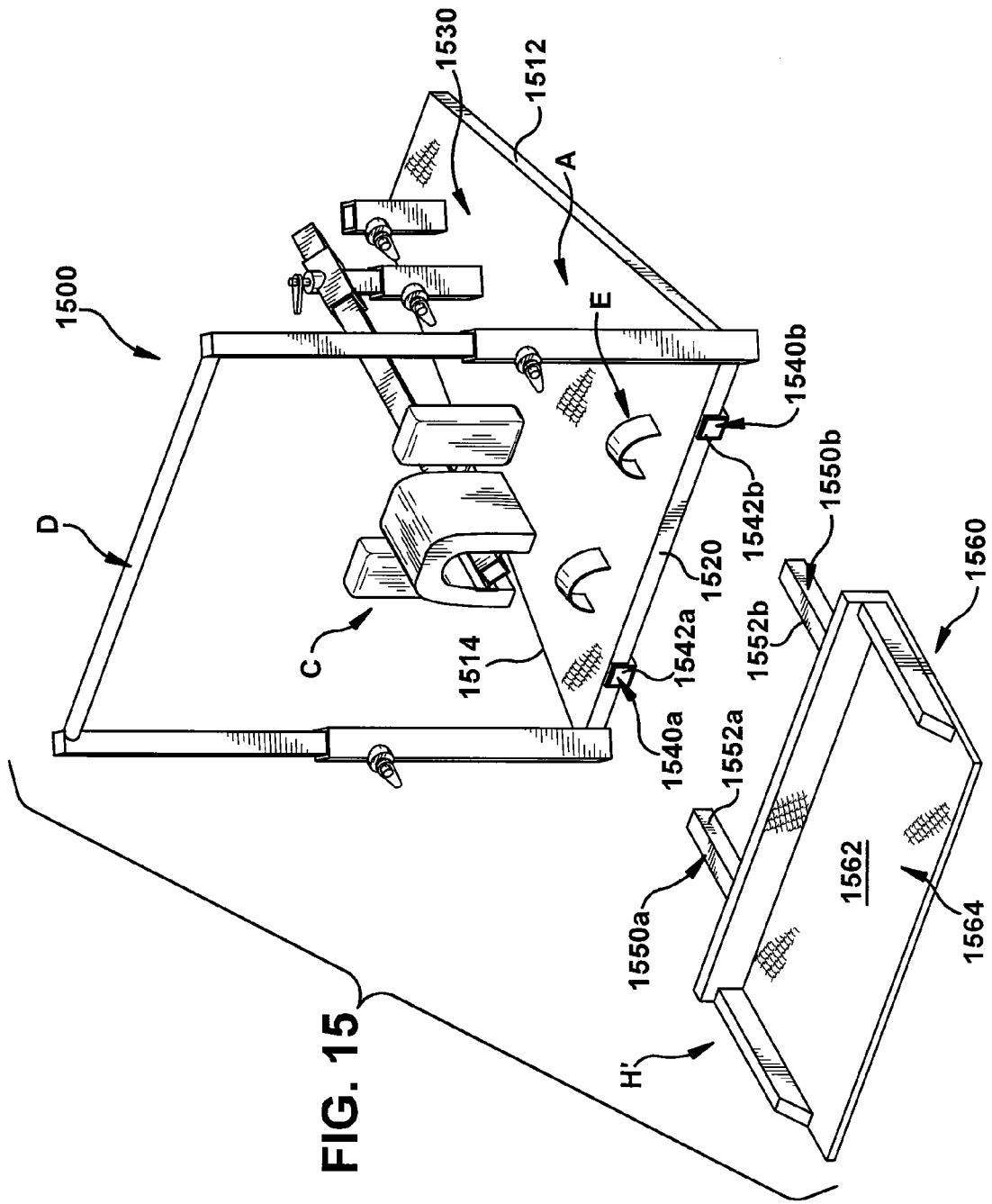
FIGS. 15 and 15a are perspective views of a therapeutic exercise apparatus in accordance with a further embodiment including a wheelchair docking system.
Figure 15A:
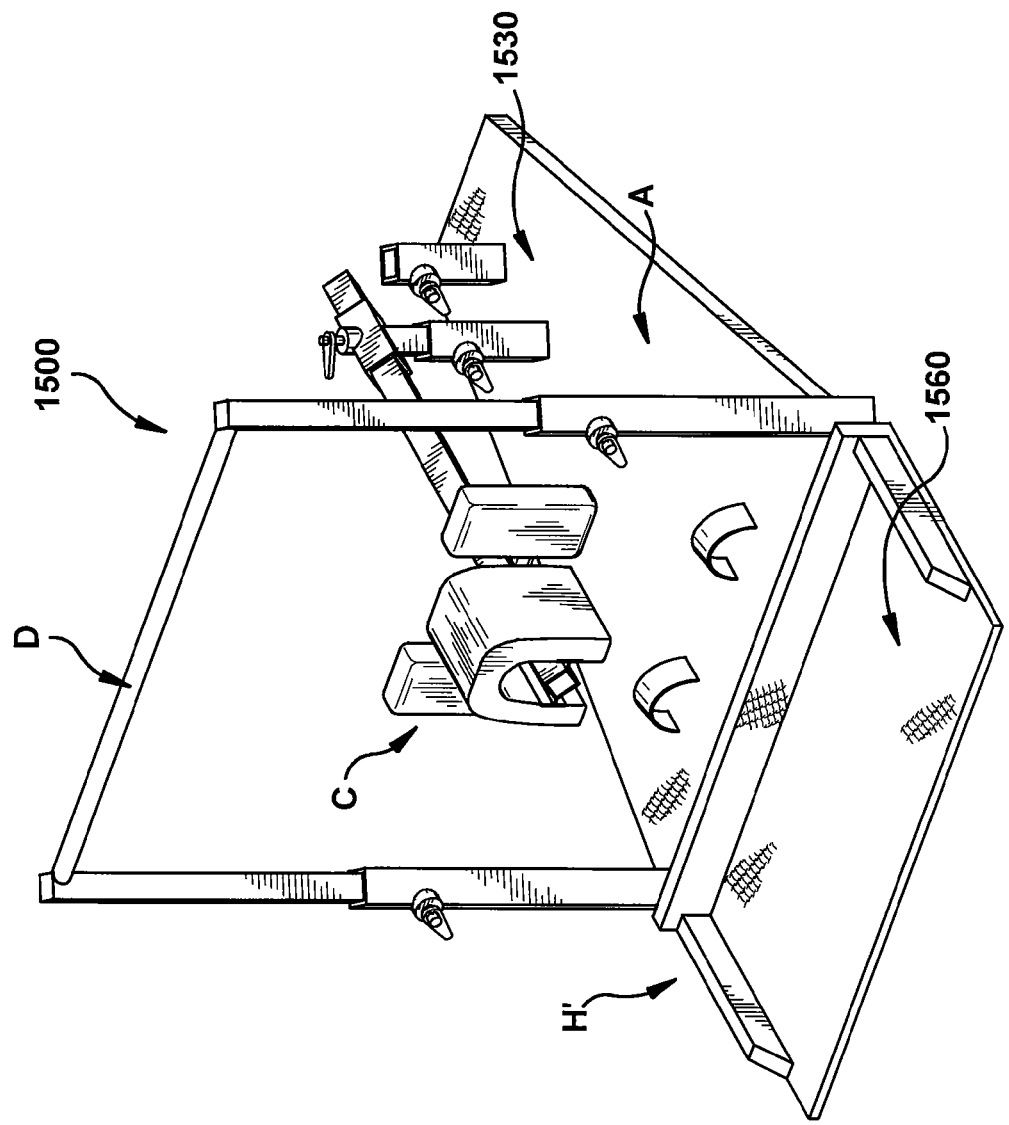

FIGS. 15 and 15a illustrate a further example embodiment of a therapeutic exercise system 1500 in accordance with a further embodiment. As shown there, a therapeutic exercise apparatus 1500 is configured as a docking station H' suitable for a wheelchair bound user. This embodiment comprises a base portion A configured to hold stirrups E, a handlebar D, and a support structure for holding a knee spreader C. In particular embodiments, the knee spreader C includes a patella pad as illustrated herein. The base portion A in this embodiment includes a triangular shaped central base member 1510 having outer left 1512 and right 1514 edges and a forward lead edge 1520. The outer edges define a truncated wedge 1530 configured to provide stability to the system 1500. The forward lead edge 1520 includes a set of first surfaces 1540a, 1540b configured to assist in guiding an associated set of second surfaces 1550a, 1550b of a wheelchair support member 1560 into selective coupled engagement therewith. In the example embodiment illustrated, the first surfaces 1540a, 1540b are elongate recesses 1542a, 1542b defined in the forward lead edge 1520 and the second surfaces 1550a, 1550b are elongate posts 1552a, 1552b configured for selective slidable engagement into the elongate recesses 1542a, 1542b. In an example embodiment, selected portions of a top surface 1562 of the wheelchair support member 1560 is coated with a friction enhancing material 1564 such as an adhesive backed sandpaper or a grit impregnated in a coating substance. The friction enhancing coating helps hold the wheelchair in a substantially fixed position relative to the apparatus during use in therapy and/or training.

Figure 16:
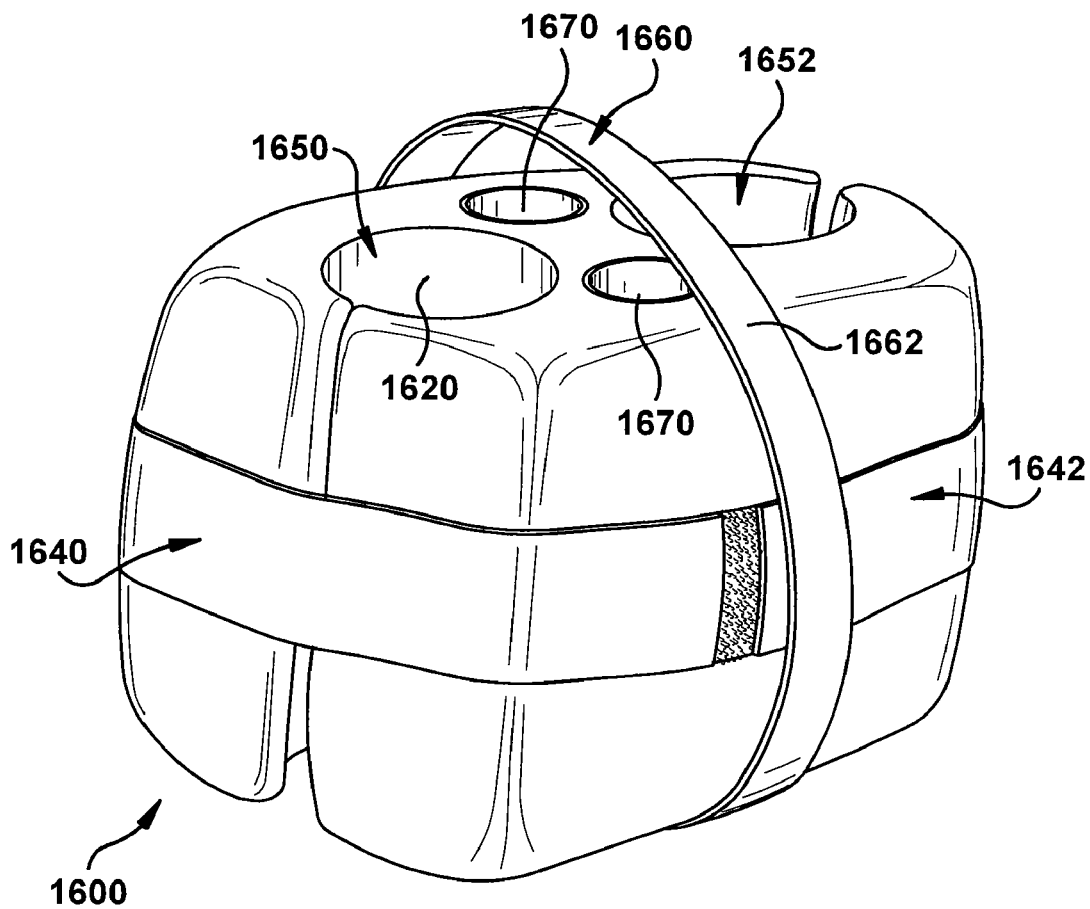
FIG. 16 is a perspective view of a transfer block apparatus for stabilizing the knees of a user during exercise on the therapeutic exercise apparatus of FIGS. 9 and 9a, and during transport of the user.
Figure 16A:
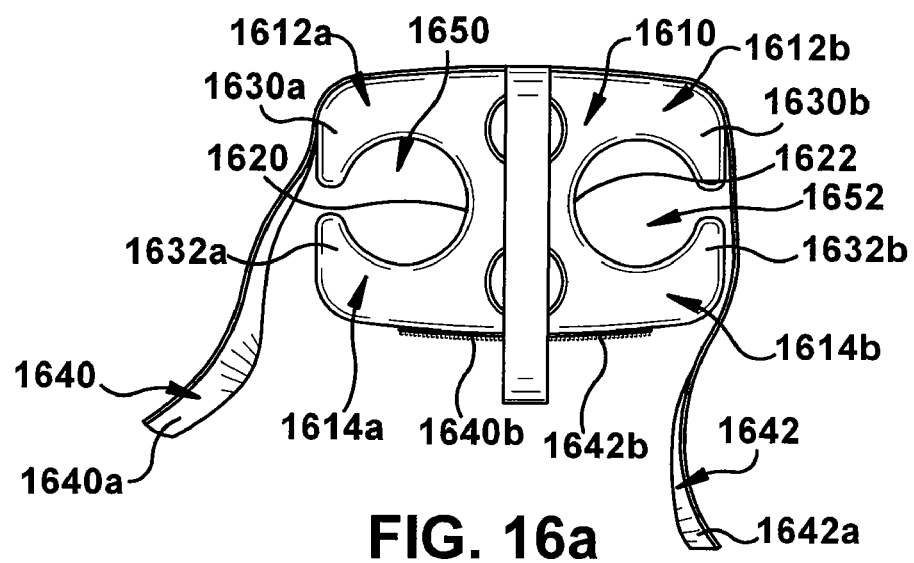
FIG. 16a is a top view of a transfer block apparatus of FIG. 16.
Figure 16C:
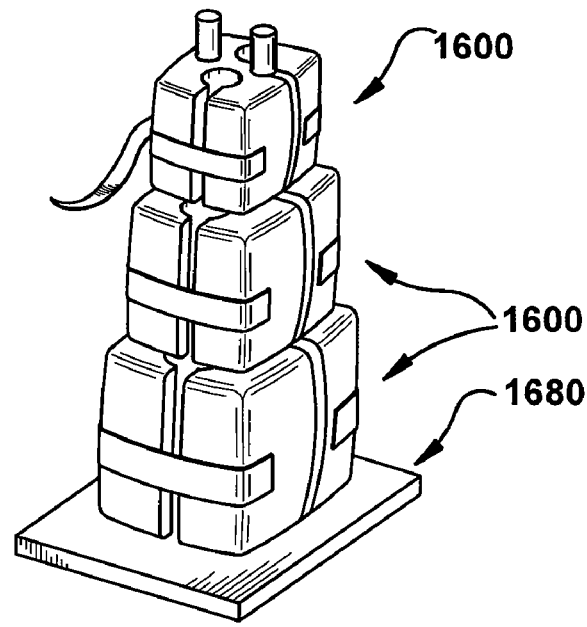
FIG. 16c is a perspective view of a set of transfer block apparatus of FIG. 16 illustrated on a storage rack.
Figure 16B:
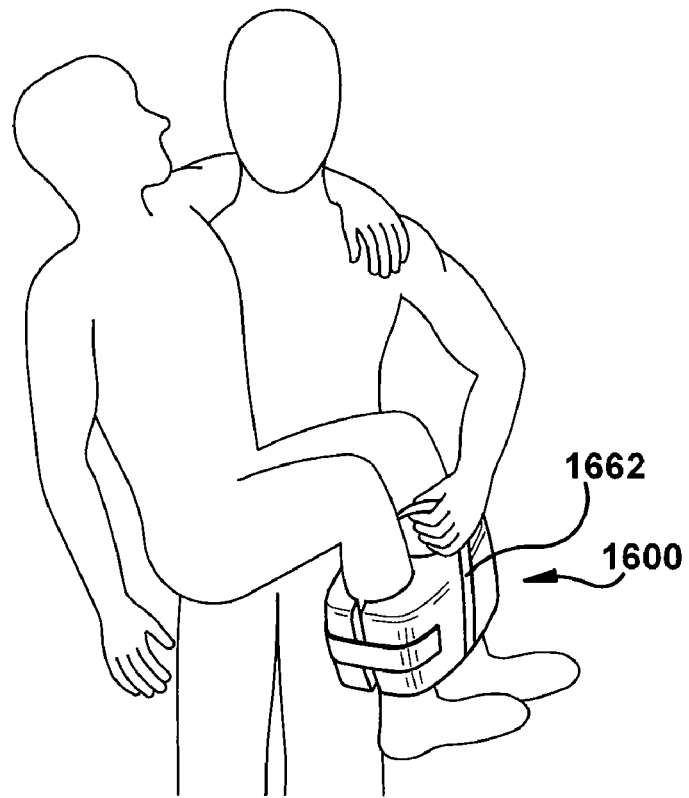
FIG. 16b is a perspective view of a transfer block apparatus of FIG. 16 during use in transporting a user illustrated with a user and with an assistant.

FIGS. 16 and 16a are a perspective and top view respectively, of a further example embodiment of a training ball 900' such as shown in FIGS. 10, 10a, and 10b described above. As illustrated, the training ball 900' is a generally spheroid device 1600 including a central body portion 1610 with anterior 1612 and posterior 1614 leg stabilizing members extending outwardly from the central body portion 1610. In one preferred form, the ball is made of foam but it may also be made of plastic or foam covered with a rubberized material or the like. Further, the ball may be formed of an inflatable bladder like member having, when inflated to a predetermined pressure, an overall shape and configuration such as illustrated in the Figures. In the example embodiment, the central body portion has opposite first 1620 and second 1622 ends, the first end 1620 is configured to engage an inside portion of a first leg of the associated user (FIG. 16b), and the second end 1622 is configured to engage an inside portion of a second leg of the associated user (FIG. 16b). The anterior leg stabilizing members 1612 extend generally outwardly from the first and second ends of the central body portion 1610. A first anterior leg stabilizing member 1612a is configured to engage an anterior leg portion of the first leg of the associated user, and the second anterior leg stabilizing member 1612b is configured to engage an anterior leg portion of the second leg of the associated user. Similarly, a first posterior leg stabilizing member 1614a is configured to engage a posterior leg portion of the first leg of the associated user and a second posterior leg stabilizing member 1614b is configured to engage a posterior leg portion of the second leg of the associated user. In the example embodiment, the central body portion 1610 and the anterior 1612 and posterior 1614 leg stabilizing members collectively hold the knees of the associated user in a splayed relative orientation such as illustrated in FIG. 16b.

FIGS. 16 and 16a further illustrate outer leg stabilizing members 1630 and 1632 operatively coupled with the central body portion. A first set of outer leg stabilizing members 1630a, 1632a are configured to cooperatively engage an outside leg portion of the first leg of the associated user and hold the first leg of the associated user against the first end 1620 of the central body portion 1610. Similarly, a second set of outer leg stabilizing members 1630b, 1632b are configured to engage an outside leg portion of the second leg of the associated user and hold the second leg of the associated user against the second end 1622 of the central body portion 1610.

A first set of straps 1640 are provided on one side of the central body portion 1610 and, together with a second set of straps 1642 provided on the other side of the central body portion 1610 are configured to selectively assist in affixing the ball 900' to the legs of the user below the knees such as shown in FIG. 16b. The free ends 1640a, 1642a of the straps 1640, 1642 carry a first portion of a loop and hook fastener and the outer surface of the body 900' carries the complementary portion of the loop and hook fastener system 1640b, 1642b whereby the straps may be selectively opened to permit the reception of the user's legs into elongate channels 1650, 1652 defined in the body, and selectively releasably mutually attached for securing the user's legs in the channels for holding the knees in the splayed orientation such as shown in FIG. 16b.

In addition, the training and transport ball 1600 includes a handle 1660 for gripping the device such as shown in FIG. 16b when transporting the user from place to place. The handle 1660 is preferably in the form of a flexible strap 1662 surrounding the body of the block in a direction transverse the major direction of the leg securing straps 1640, 1642. Still further, the main body includes strength reinforcing members 1670 extending substantially in parallel with the longitudinal axes defined by the leg passageways for strengthening the apparatus so that users of varying sizes can be carried. The strength reinforcing members 1670 are also useful in providing for a plurality of blocks to be stored in a stacked arrangement on an associated storage rack 1680 such as shown in FIG. 16c for example.

Described above are example embodiments. It is, of course, not possible to describe every conceivable combination of components or methodologies for purposes of describing the example embodiments, but one of ordinary skill in the art will recognize that many further combinations and permutations of the example embodiments are possible. Accordingly, it is intended to embrace all such alterations, modifications and variations that fall within the spirit and scope of any claims filed in applications claiming priority hereto interpreted in accordance with the breadth to which they are fairly, legally and equitably entitled.

The invention claimed is:

1. An exercise apparatus comprising:
a base member having a longitudinal axis;
an upstanding support member extending from the base member at a first position on the longitudinal axis;
a seat mounted relative to the upstanding support member, the seat being configured to support the buttocks of an associated user of the exercise apparatus relative to the base member;
a handrail extending from the base member and including a grippable portion located above the seat at a second position on the longitudinal axis spaced from the first position on the longitudinal axis;
a cushion operatively attached with the seat and being configured to engage the legs of the associated user of the exercise apparatus, the cushion being selectively movable relative to the seat in a direction parallel to the longitudinal axis; and,
stirrups mounted on the base in a spaced apart relationship on opposite sides of the longitudinal axis of the base member, the stirrups being configured to hold the feet of the associated user of the exercise apparatus in a substantially fixed relationship relative to the base member so that the knees of the associated user are splayed out by the cushion while using the apparatus by selectively gripping on the grippable portion of the handrail and moving relative to the seat by standing and sitting.

2. The exercise apparatus according to claim 1 further comprising:
a seat positioning apparatus configured to position the seat by the upstanding support member at a selected one of a plurality of positions relative to the base member.

3. The exercise apparatus according to claim 2, wherein the seat positioning apparatus comprises:
an interface member carried by the seat and being adapted for coupling the seat with the upstanding support member; and,
a locking device for selectively holding the interface member at selectable positions relative to the upstanding support member.

4. The exercise apparatus according to claim 3, wherein:
the interface member comprises an elongate member configured to telescopically engage the upstanding support member for slidably coupling the seat with the upstanding support member; and,
the locking device somprises fixing means including a one of a pin or a clamp for selectively holding the interface member at the selectable positions relative to the upstanding support member.

5. The exercise apparatus according to claim 2, wherein the seat defines a partial spherical surface.

6. The exercise apparatus according to claim 5, further comprising:
a hinged connector for connecting the seat with the adjustable positioning means, the hinged connector defining a transverse pivot axis substantially perpendicular to the longitudinal axis wherein the partial spherical surface of the seat is selectively movable in an arc about the pivot axis.

7. The exercise apparatus according to claim 2, further comprising:
a coupling member extending between the seat and the cushion, the coupling member carrying the cushion relative to the seat and permitting relative selective movement between the cushion and the seat in the direction parallel to the longitudinal axis.

8. The exercise apparatus according to claim 7, further comprising:
a locking device for holding the cushion at a selected position relative to the seat.

9. An exercise apparatus comprising:
a base member having a longitudinal axis;
an upstanding support member extending from the base member at a first position on the longitudinal axis;
a cushion operatively attached with the support member and being configured to engage the legs of an associated user of the exercise apparatus, the cushion being located relative to the support member at a second position on the longitudinal axis;
a handrail extending from the base member and including a grippable portion located above the cushion at a third position on the longitudinal axis spaced from the first and second positions on the longitudinal axis;
a user support member operatively coupled with the base member and adapted to rest stably on an associated support surface, the user support member being disposed at a fourth position on the longitudinal axis spaced from the second position opposite the first position and having spaced apart longitudinal foot support sections extending substantially in parallel with the longitudinal axis, each of the foot support sections for receiving a foot of the associated user in a substantially fixed relationship relative to the user support member while the associated user is positioned adjacent the exercise apparatus so that the knees of the associated user are splayed out by the cushion while using the apparatus by the associated user selectively gripping on the grippable portion of the handrail and moving by standing and sitting relative to the user support member.

10. The exercise apparatus according to claim 9 wherein:
the foot support sections include stirrups mounted on the user support member in a spaced apart relationship on opposite sides of the longitudinal axis, the stirrups being configured to loop around and hold the feet of the associated user of the exercise apparatus in the substantially fixed relationship relative to the user support member so that the knees of the associated user are splayed out by the cushion while using the apparatus by the associated user selectively gripping on the grippable portion of the handrail and moving by standing and sitting relative to the user support member.

11. The exercise apparatus according to claim 10 further comprising:
a seat mounted relative to the upstanding support member on the longitudinal axis at a fifth position between the first position and the handrail, the seat being configured to support the buttocks of an associated therapist second user of the exercise apparatus.

\* \* \* \* \*